United States Patent [19]
Buck et al.

[11] Patent Number: 5,521,221
[45] Date of Patent: May 28, 1996

[54] RETRO-α-RETINOL (4,14-RETRO-RETINOL) DERIVATIVES AND USES OF RETRO-α-RETINOL

[75] Inventors: Jochen Buck; Ulrich Hammerling; Fadila Derguini; Koji Nakanishi, all of New York, N.Y.

[73] Assignees: Sloan-Kettering Institute for Cancer Research; The Trustees of Columbia University in the City of New York, both of New York, N.Y.

[21] Appl. No.: 682,909

[22] Filed: Apr. 9, 1991

[51] Int. Cl.⁶ .................... C07C 35/18; C07C 37/68
[52] U.S. Cl. .................... 514/725; 435/155; 435/244; 514/715; 514/519; 514/546; 514/613; 514/763; 568/822; 568/823; 568/824; 568/828
[58] Field of Search .................... 568/824, 822, 568/823, 715; 514/729, 763, 15, 613, 616, 659, 715, 519, 546; 435/122.3, 244

[56] References Cited

U.S. PATENT DOCUMENTS

| | | | |
|---|---|---|---|
| 4,825,006 | 4/1989 | Otera et al. | 568/824 |
| 4,906,795 | 3/1990 | Grosselin et al. | 568/824 |

OTHER PUBLICATIONS

Garbe et al, "Chemical Abstracts", vol. 117 (9) p 88604t (1992)

Buck et al, "Chemical Abstracts", vol. 116 p 104269z (1992).

*Primary Examiner*—Werren B. Lone
*Attorney, Agent, or Firm*—John P. White

[57] ABSTRACT

This invention provides a purified retro-retinoid compound characterized by a molecular mass of about 302 daltons. Also provided by this invention is a method of enhancing the growth of a cell in a vitamin A reduced environment which comprises contacting the cell with an effective growth enhancing amount of a compound having a structure:

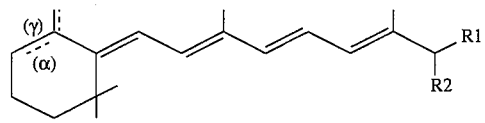

wherein the configuration of the C6, C8, C10 and C12 double bond independently is Z or E and the absolute configuration at C-14 is independently R or S; wherein $R_1$ is alkyl, alkyl halide, alcohol, ester, ether, aldehyde, ketone, carboxylic acid, carboxylic ester, acid halide, amide, nitrile, or amine; and wherein $R_2$ is hydroxyl, halide, alkoxy, ester, alkyl, alcohol, ether, aldehyde, ketone, carboxylic acid, carboxylic ester, nitrile, amine, azide, alkyl halide, acid halide, acid azide, or amide; or wherein $R_1$ and $R_2$ are replaced by a 14, 15-oxirane group; and wherein the retro structure is alpha or gamma. Further provided are a method for enhancing transcription of a gene regulated by retinoid in a cell, or a method for enhancing an immune response in a subject.

4 Claims, 23 Drawing Sheets

RETINOL

ALL TRANS RETINOIC ACID

RO10-1670 (ETRETINE)

RO 13-7410 (TTNPS)

RO 40-6055 (AM 80)

NO RETINOL $10^{-6}$ M RETINOL

RETRO-α-RETINOID

NORMAL (OR β-) RETINOID

RETRO-γ-RETINOID

RETRO-α-RETINOL (4,14-RETRO-RETINOL) DERIVATIVES AND USES OF RETRO-α-RETINOL

The invention described herein was made in the course of work under Grant Number CA 499 33 from the United States Government. The United States Government has certain rights in this invention.

BACKGROUND OF THE INVENTION

Throughout this application various publications are referenced to by arabic numeral within parenthesis. Full bibliographic citations for these references may be found at the end of the specification immediately preceding the claims. The disclosures for the publications in their entireties are hereby incorporated by reference into this application to more fully describe the state of the art to which this invention pertains.

It has long been known that dietary restriction of vitamin A causes widespread abnormalities in tissue and organ physiology, especially in neonates. The vitamin A deficiency syndrome is characterized by generally stunted growth, keratoses of skin and eyes (1) (leading in severe cases to blindness), defective testis development (2) etc., and atrophy of central (i.e., thymus and bursa of Fabrizius) and peripheral lymphoid organs. Consequently, immune functions are severely affected. Even in mild cases of vitamin A deficiency, the immune system appears to be hyporesponsive. In a recent study in southern India (4), the authors noted in children suffering from mild vitamin A deprivation significantly higher mortality rates in common childhood diseases compared with children receiving normal dietary levels of vitamin A. Since severity but not susceptibility to infection was correlated with vitamin A deprivation, it is likely that reduced immune functions are a factor.

In the absence of retinol, lymphoblastoid cells (LCL) die within 24 to 48 hours. (5) Retinol and retinaldehyde, but not retinoic acid, support the growth of LCL in serum-free medium. The same is true for activated human thymocytes. These finding may represent direct correlates to the lagging development of lymphoid organs described by Wolbach and Howe (3) and the in-vivo immune system dysfunction referred to earlier. (4)

Nearly all vertebrate tissues are bathed in a constant supply of vitamin A, and the ubiquitous distribution of cellular retinol-binding protein (CRBP) with its high affinity to retinol suggests that it is inside most cells as well. Yet the general purpose of retinol, its metabolism and final destination, remain for the most part unknown, the well-studied example of specialized usage such as vision notwithstanding. Since retinal is not known to be incorporated into structural parts of cells and does not bind to one of the yet analyzed transcription factors with high enough affinity, its role is more likely to be found in its function as precursor for derivatives. Use of retinaldehyde in vision is one example, and another that of retinoic acid as a morphogen (6), important for development of limb and brain. When coupled with parallel discoveries of retinoic acid receptors (RAR) (7A-7C) within the larger steroid receptor superfamily (8), a sound molecular foundation is given. In this hypothesis, RARs bind to specific response elements in the promoter regions of genes. Retinoic acid in turn binds to RAR, causing activation of gene transcription. The universal principle of this genetic control has increasingly been highlighted by observations that many developmentally important genes from drosophila to man are part of the retinoic acid/steroid receptor superfamily. Moreover, for more than two dozen "orphan receptors" (9) engaged in control of the general physiology of cells, the ligands are not known and are suspected to be small lipophilic molecules.

In analogy to retinoic acid, other members of the retinoid family may also serve as transcriptional activators. This concept has been pursued in the current invention leading to the discovery of retinoid molecule hitherto unknown in nature, that can activate certain physiological processes in β lymphocytes. This new compound, 14-hydroxy- 4,14-retro-retinol (14-hydroxy-retro-α-retinol) may work along a pathway parallel to the well established retinoic acid pathway, but leading to distinct physiological responses.

SUMMARY OF THE INVENTION

This invention provides a purified retro-retinoid compound characterized by a molecular mass of about 302 daltons. Also provided by this invention is a method of enhancing the growth of a cell in a vitamin A reduced environment which comprises contacting the cell with an effective growth enhancing amount of a compound having a structure:

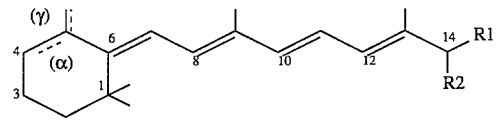

wherein the configuration of the C6, C8, C10 and C12 double bond independently is Z or E and the absolute configuration at C-14 is independently R or S; wherein $R_1$ is alkyl, alkyl halide, alcohol, ester, ether, aldehyde, ketone, carboxylic acid, carboxylic ester, acid halide, amide, nitrile, or amine; and wherein $R_2$ is hydroxyl, halide, alkoxy, ester, alkyl, alcohol, ether, aldehyde, ketone, carboxylic acid, carboxylic ester, nitrile, amine, azide, alkyl halide, acid halide, acid azide, or amide; or wherein $R_1$ and $R_2$ are replaced by a 14, 15-oxirane group; and wherein the retro structure is alpha or gamma.

This invention further provides a method for enhancing transcription of a gene regulated by retinol in a cell which comprises contacting the cell with an effective transcription-enhancing amount of a compound having the structure:

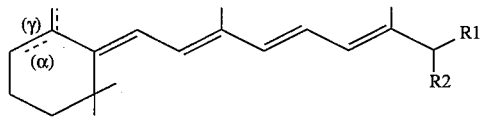

wherein the configuration of the C6, C8, C10 and C12 double bond independently is Z or E and the absolute configuration at C-14 is independently R or S; wherein $R_1$ is alkyl, alkyl halide, alcohol, ester, ether, aldehyde, ketone, carboxylic acid, carboxylic ester, acid halide, amide, nitrile, or amine; and wherein $R_2$ is hydroxyl, halide, alkoxy, ester, alkyl, alcohol, ether, aldehyde, ketone, carboxylic acid, carboxylic ester, nitrile, amine, azide, alkyl halide, acid halide, acid azide, or amide; or wherein $R_1$ and $R_2$ are replaced by a 14, 15-oxirane group; and wherein the retro structure is alpha or gamma.

A method for enhancing an immune response in a subject is also provided by this invention which comprises administering to the subject an effective immune-enhancing amount of a compound having the structure:

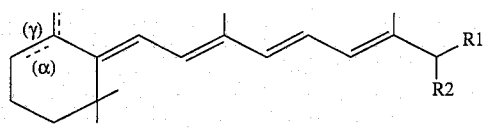

wherein the configuration of the C6, C8, C10 and C12 double bond independently is Z or E and the absolute configuration at C-14 is independently R or S; wherein $R_1$ is alkyl, alkyl halide, alcohol, ester, ether, aldehyde, ketone, carboxylic acid, carboxylic ester, acid halide, amide, nitrile, or amine; and wherein $R_2$ is hydroxyl, halide, alkoxy, ester, alkyl, alcohol, ether, aldehyde, ketone, carboxylic acid, carboxylic ester, nitrile, amine, azide, alkyl halide, acid halide, acid azide, or amide; or wherein $R_1$ and $R_2$ are replaced by a 14, 15-oxirane group; and wherein the retro structure is alpha or gamma.

BRIEF DESCRIPTION OF THE FIGURES

The file of this patent contains at least one drawing executed in color. Copies of this patent with color drawings will be provided by the Patent and Trademark Office upon request and payment of the necessary fee.

4 liters of HB101 medium were conditioned overnight with 400,000 LCL 5/2 cells/ml in HB101 medium. The medium proteins were precipitated with 80% ammonium sulfate. The proteins were freeze-dried and delipidated with ether/ethanol. 5/2 cells (1000/well) were incubated for 72 hours in HB101 medium with the indicated amounts of delipidated protein and extracted lipids. DNA synthesis was measured by [$^3$H]-thymidine uptake. The measurements were done in triplicate.

Figure 1:
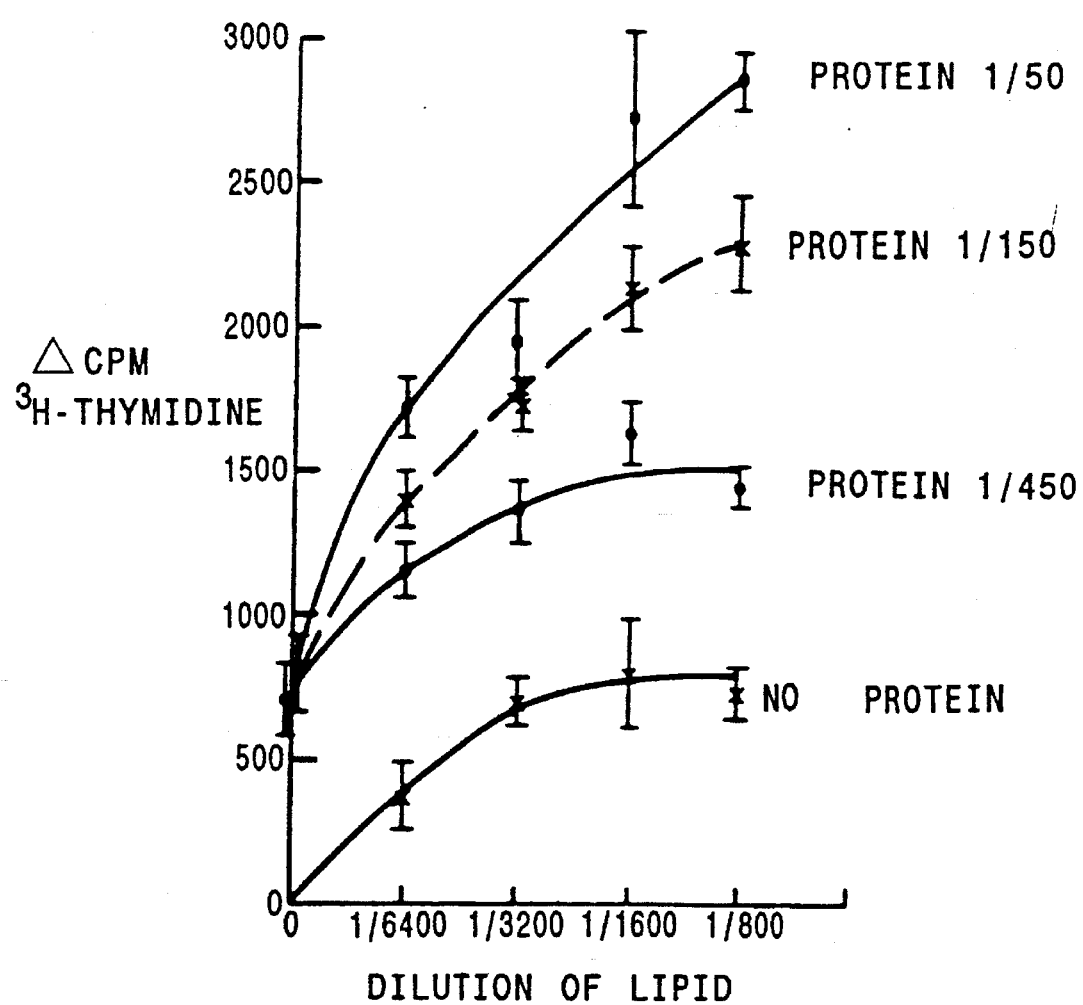
FIG. 1 shows that protein and lipids of conditioned medium are synergistic in their ability to sustain the growth of β lymphocytes.
Figure 2A:
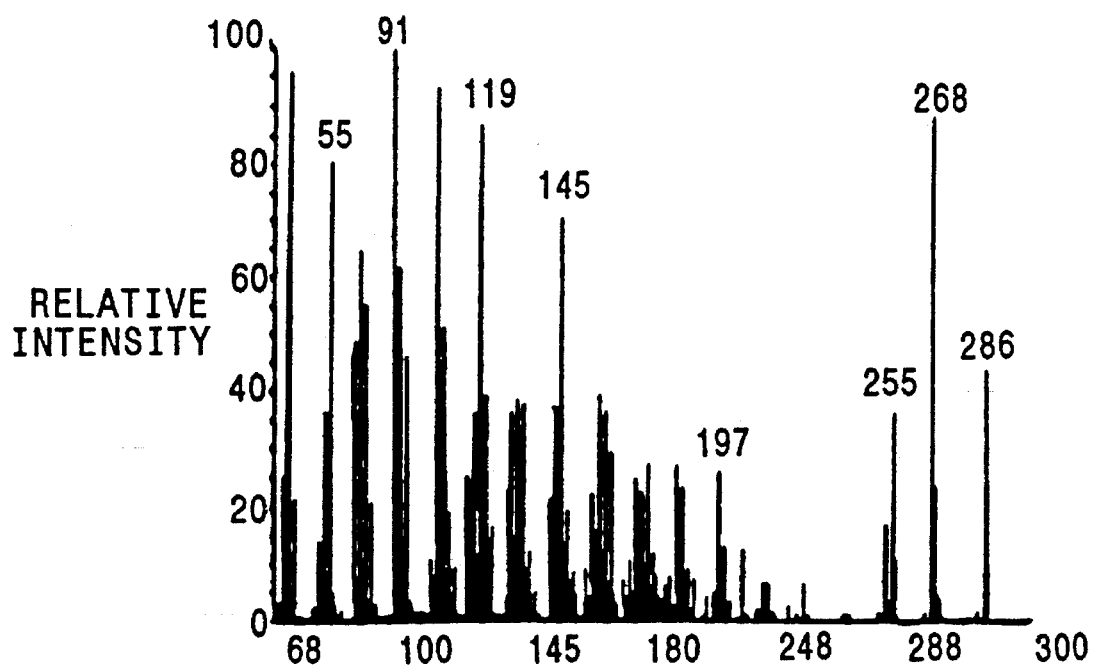

FIG. 2A is the EI mass spectrum of bioactive lipid in human serum.

Figure 2B:
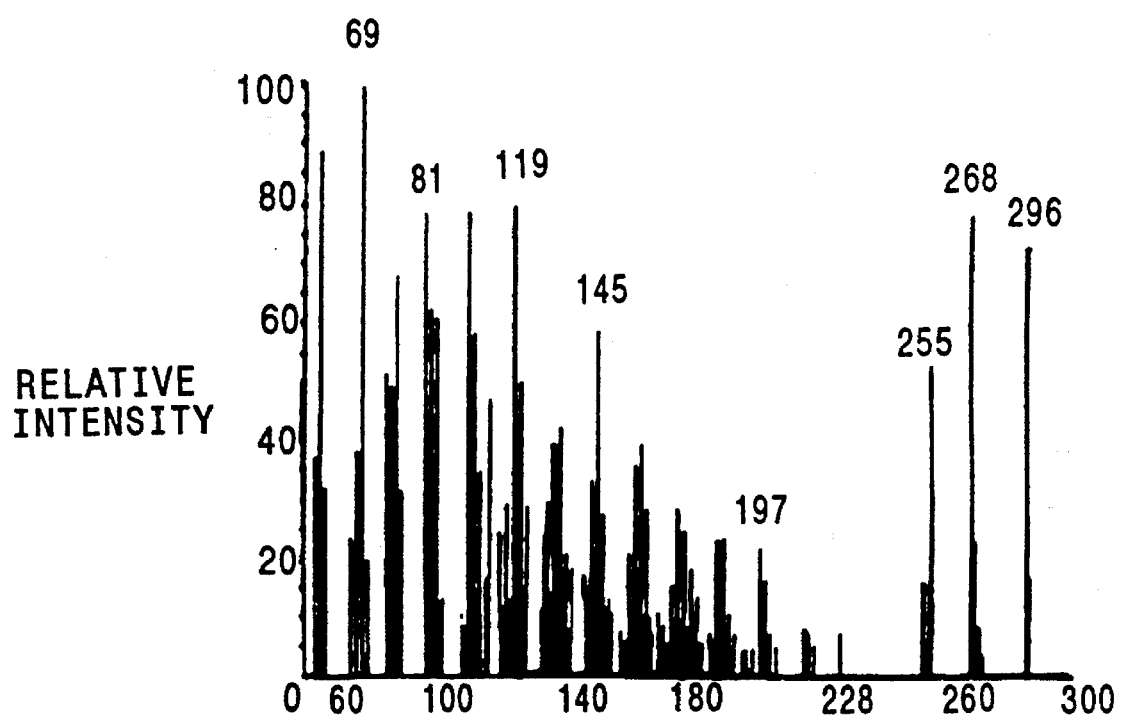

FIG. 2B is the EI mass spectrum of all-trans retinol from the National Bureau of Standards Library.

Figure 3:
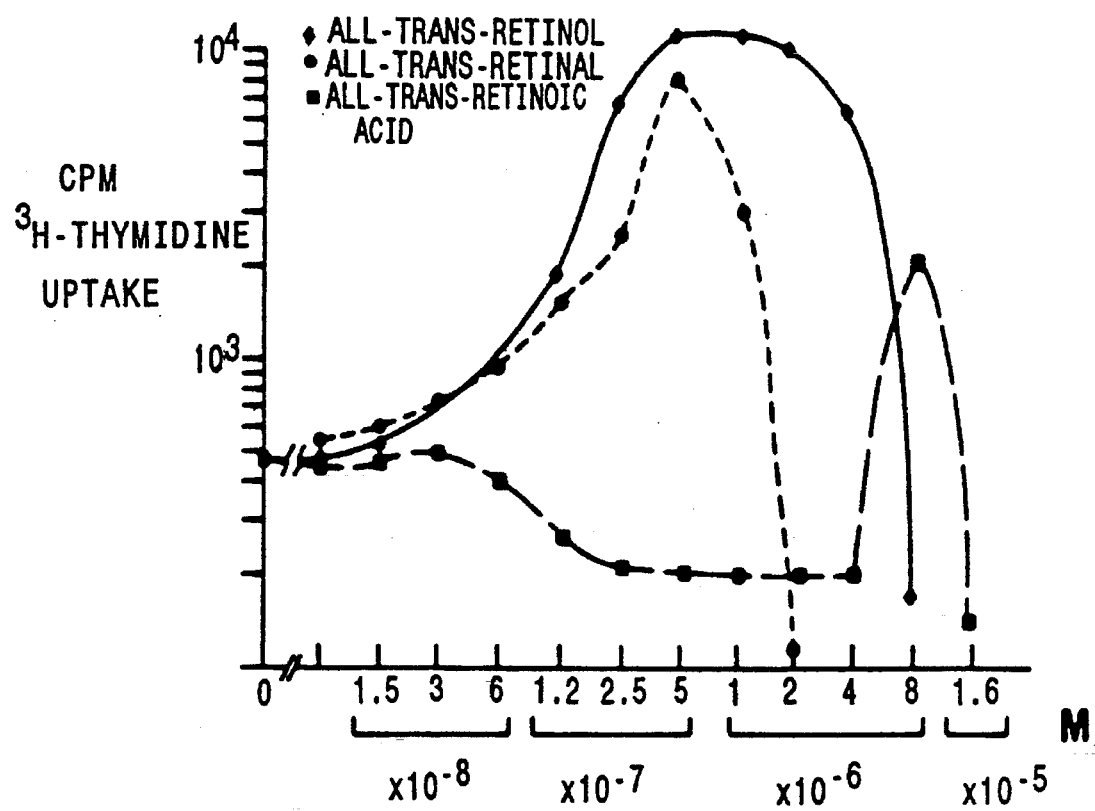

FIG. 3 shows the dose-response curves of different retinoids to stimulate the growth of 5/2 cells in culture.

Washed 5/2 cells (5,000/well) were incubated for 72 hours in HB101 medium with the indicated amounts of retinoids. DNA synthesis was measured by [$^3$H] thymidine uptake. The measurements were done in triplicate. The SDs were <15%.

FIG. 4 shows that retinol but not synthetic retinoic acid analogs enable 5/2 cells to grow.

Figure 4A:
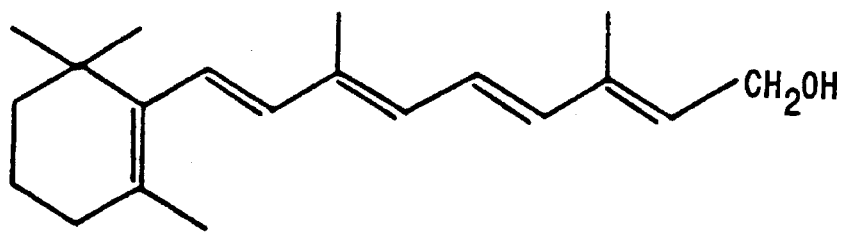
Figure 4A:
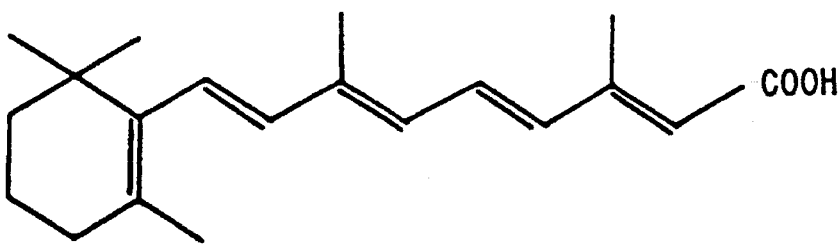
Figure 4A:
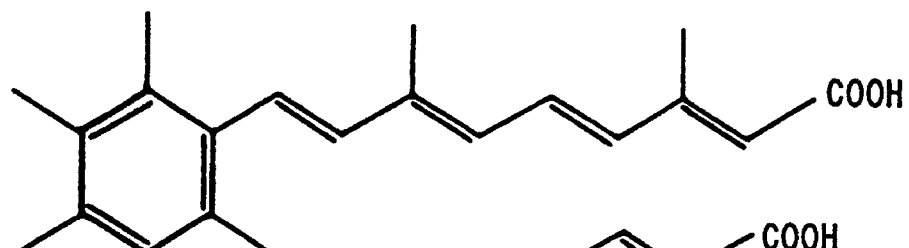
Figure 4A:
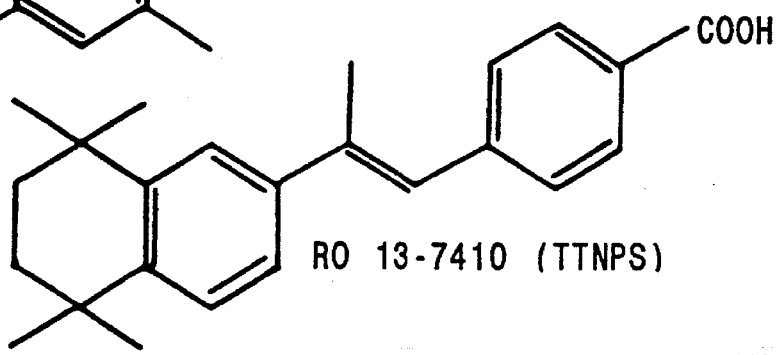
Figure 4A:
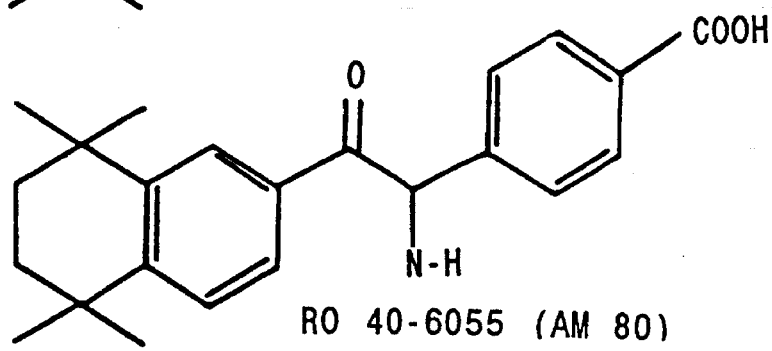

FIG. 4A is the chemical structure of retinoids used.

Figure 4B:
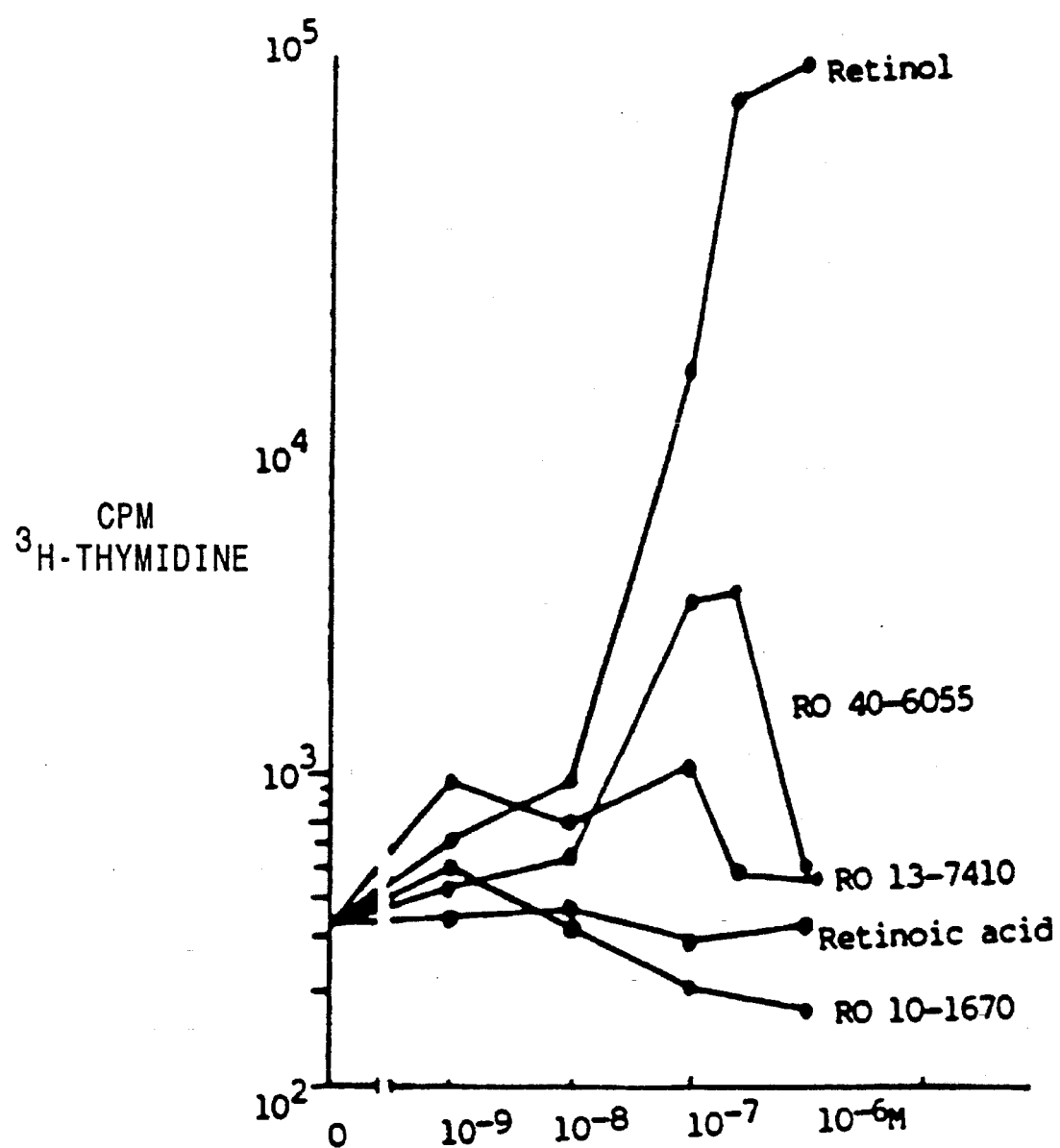

FIG. 4B is the dose-response curves measured on day 3.

Figure 4C:
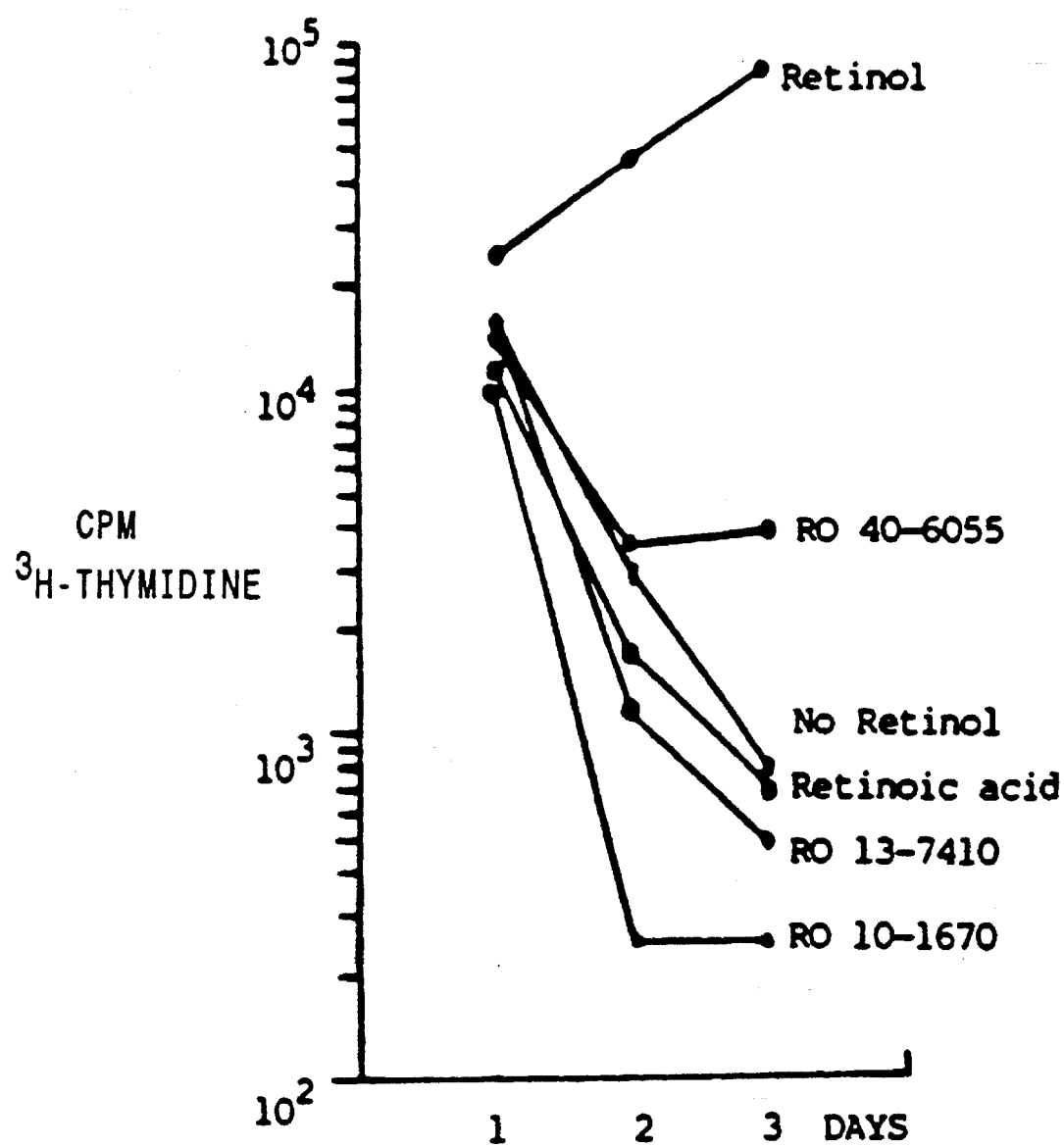
Figure 4D:
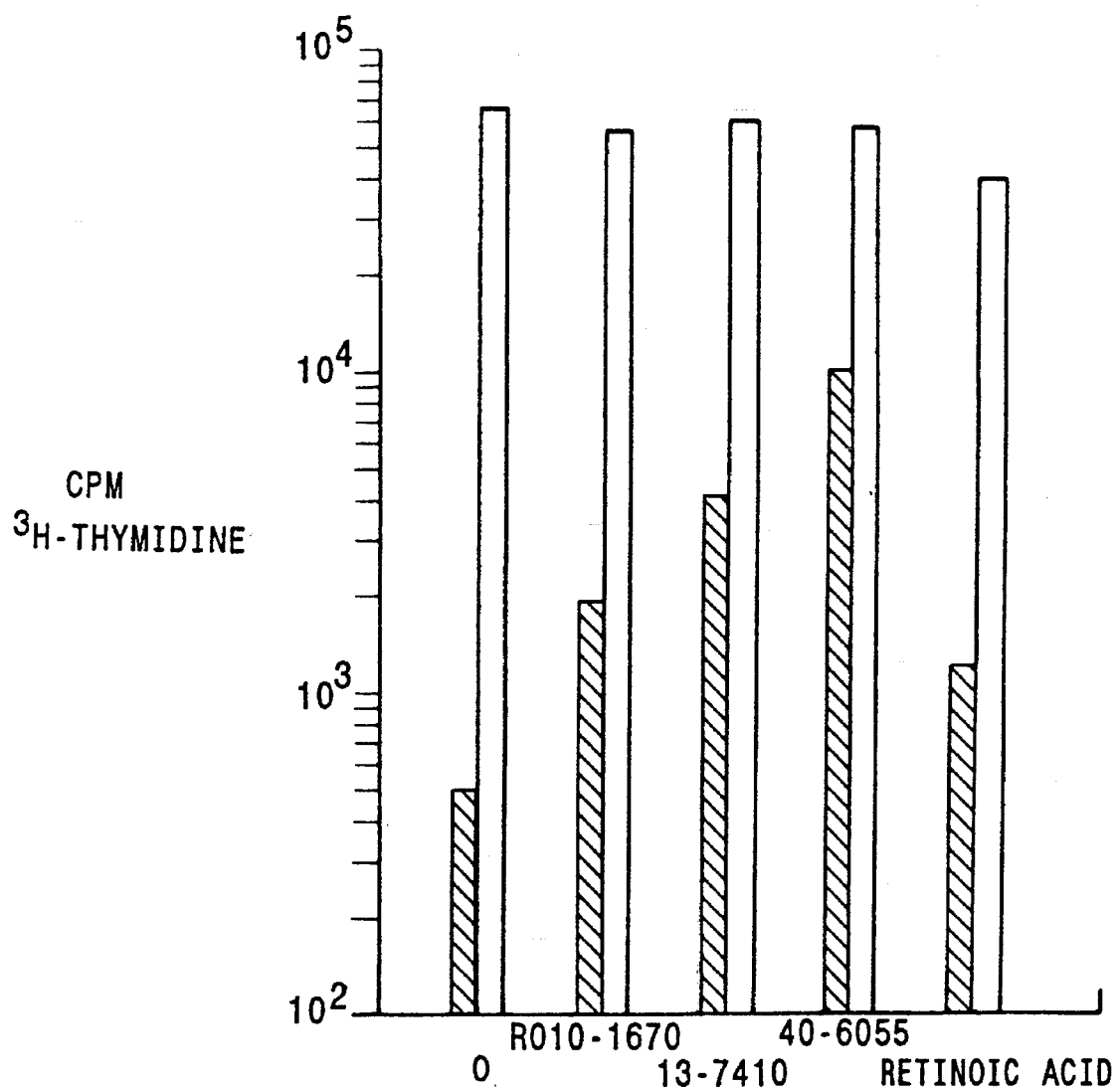

FIG. 4C shows the effect of $3 \times 10^{-7}$M retinoids measured day 1, 2 and 3. FIG. 4D shows the combination of retinoic acid analogs ($3 \times 10^{-7}$M) with and without $10^{-6}$M retinol measured on day 3. In FIGS. 4B to 4D, 5/2 cells were washed twice and seeded at a concentration of 150,000 cells/ml in HB 101 medium. Triplicate samples of 100 μl of cell suspension were removed daily and pulsed for 6 hours with [$^3$H] thymidine. Means are shown. The SDs were never >20%.

FIG. 5 shows that retinol deprivation leads to cell death.

5/2 cells were washed once and seeded at a density of 300,000/ml in HB 101 medium with and without $10^{-6}$M retinol. The trypanblue-negative (FIG. 5A) and trypanblue-positive (FIG. 5B) cell number of nine aliquots was determined every 24 hours. Means + SDs are shown. In a repeat experiment cells were stained with Wright-Giemsa stain after 40 hours of culture.

Figure 5A:
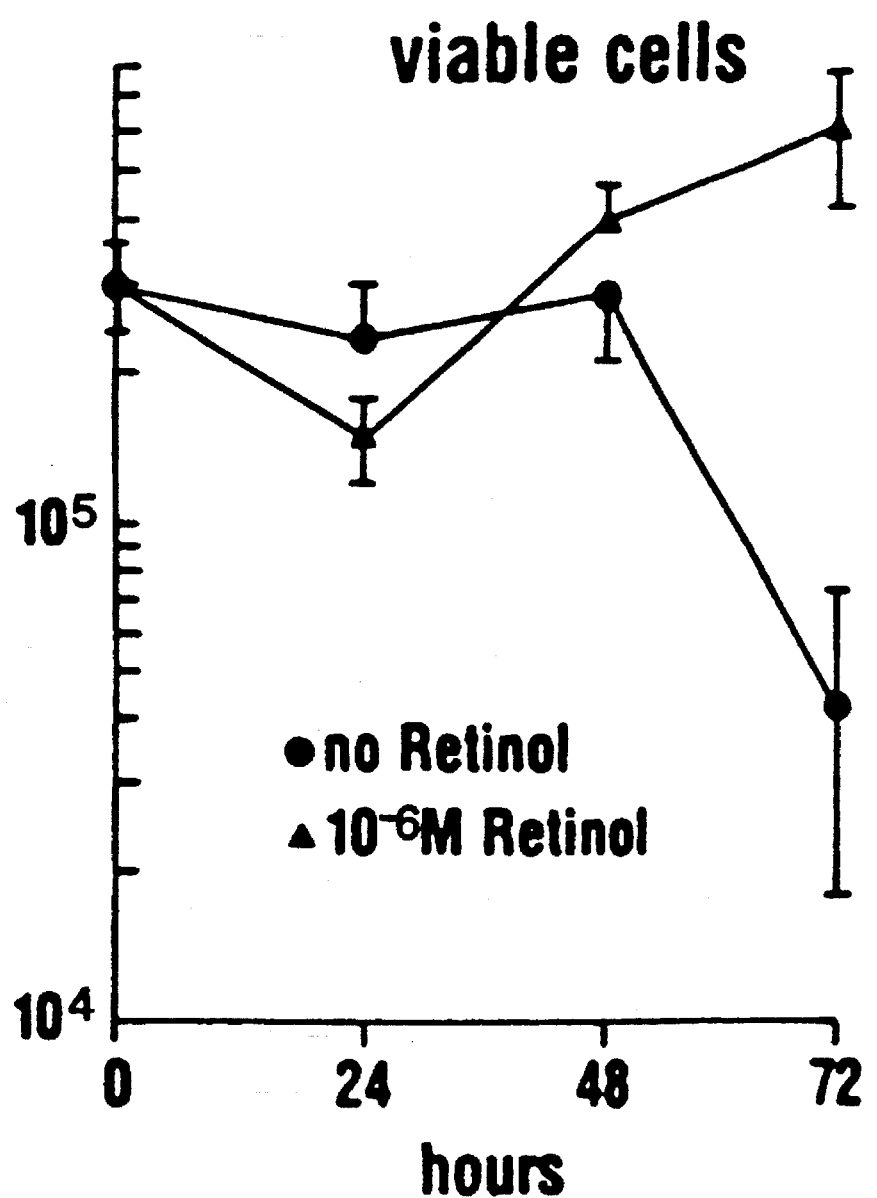
Figure 5B:
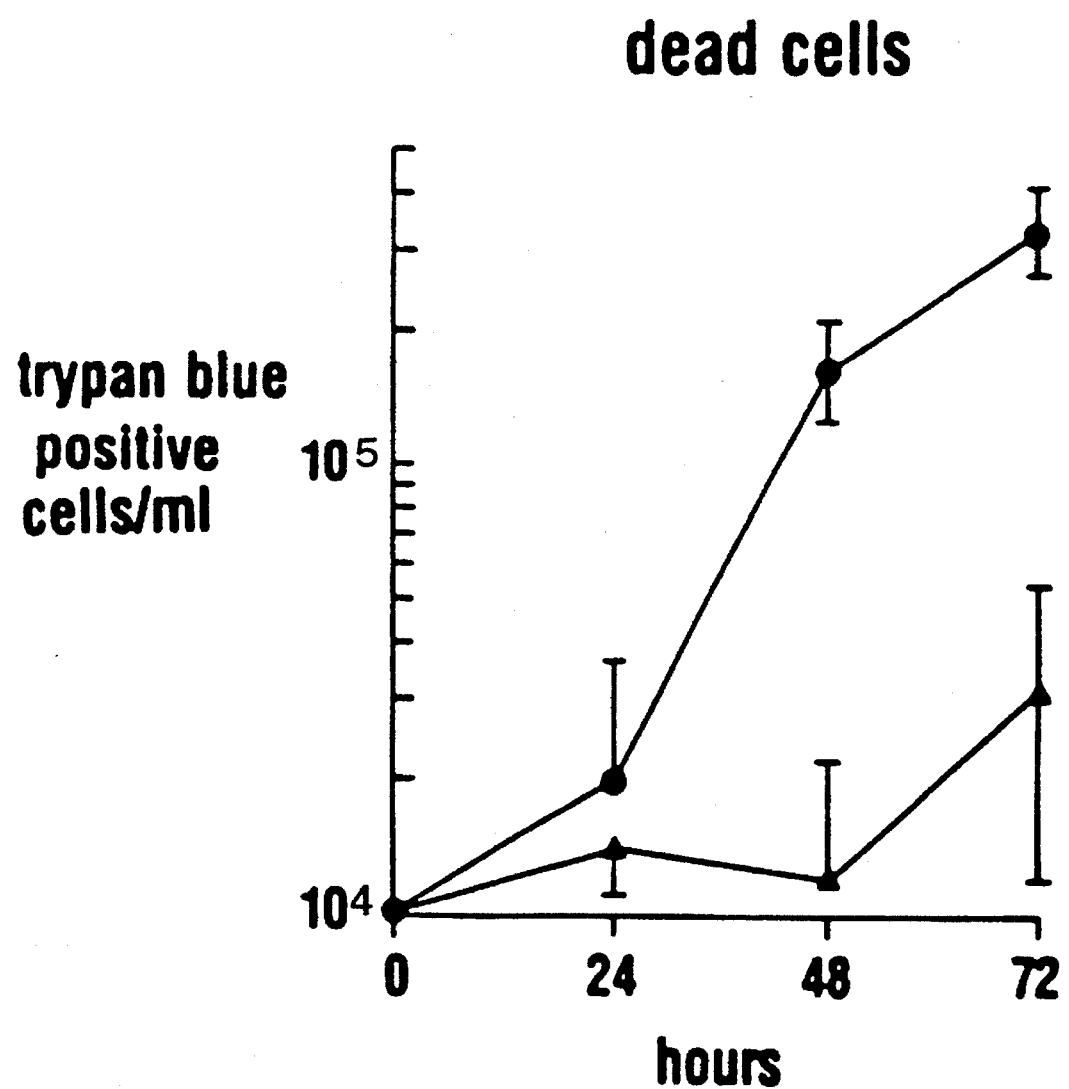
Figure 5C:
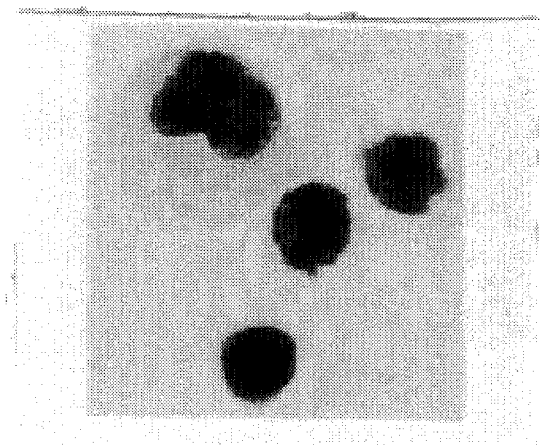

FIG. 5C shows cells without retinol.

Figure 5D:
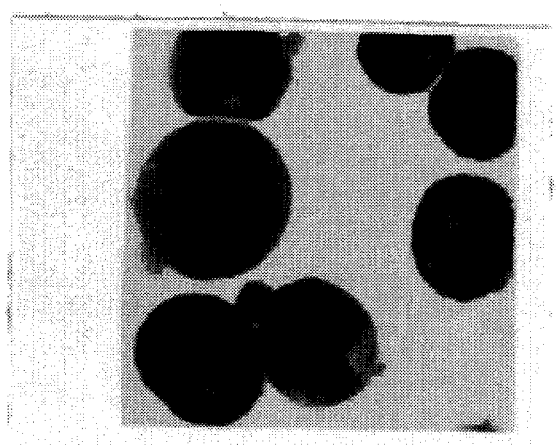

FIG. 5D shows that cells with $10^{-6}$M retinol.

Figure 6A:
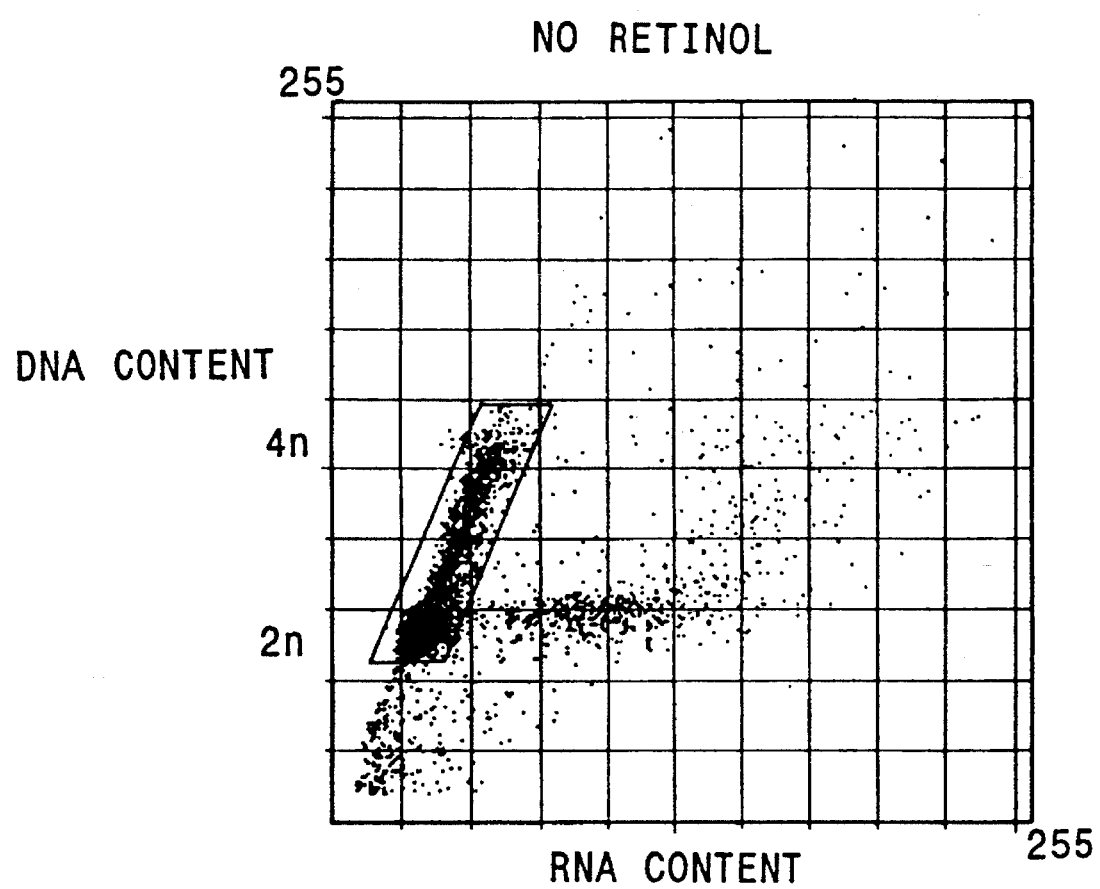
Figure 6B:
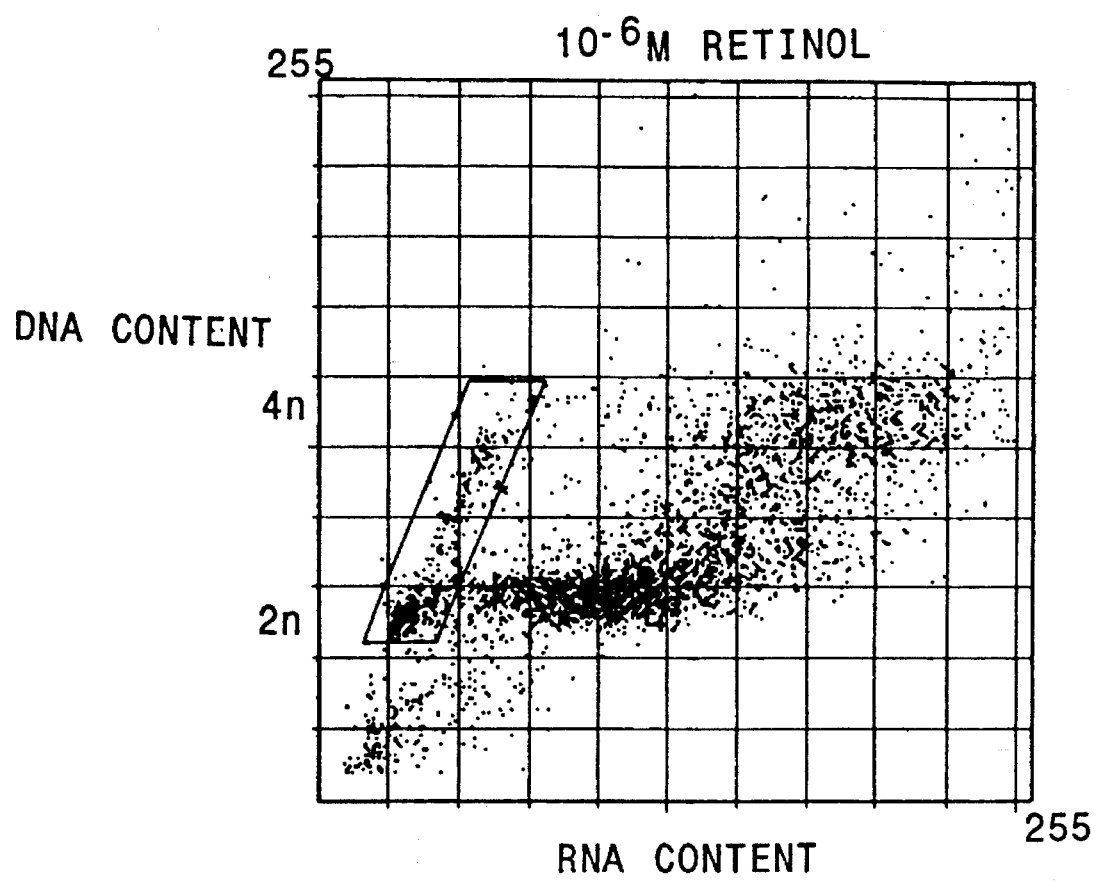

FIG. 6 shows that effect of retinol-deprivation on RNA and DNA content of 5/2 cells.

5/2 cells were washed and seeded at a density of 50,000/ml in HB 101 without (FIG. 6A) and with (FIG. 6B) $10^{-6}$M retinol. After 48 hours, the cells were stained with acridine orange and 5,000 cells/sample were analyzed by flow cytometry. Scattergrams represent distribution of cells with respect to their DNA and RNA content. 2n corresponds to diploid, 4n to tetraploid DNA content. The boxed dots with very low RNA content correspond to nuclei.

Figure 7:
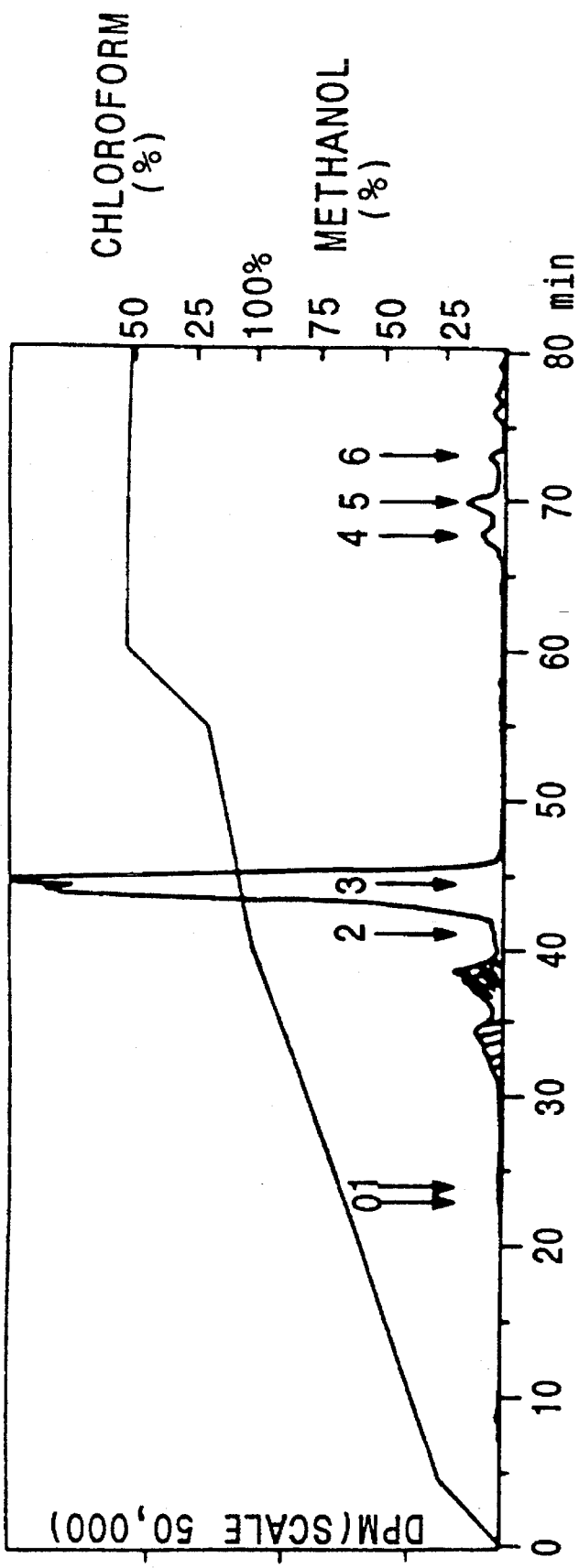

FIG. 7 shows retinol metabolites in 5/2 cells.

5/2 cells ($10^6$ cells in 10 ml HB 101 medium) were incubated with all-trans-[$^3$H] retinol (10 uCe/ml). After 24 hours, retinoids were extracted from the washed cell pellet and unlabeled marker retinoids were added. The crude extract was loaded on an analytical reversed-phase C-18 column. Retinoids were eluted with the shown linear gradient of water/methanol/chloroform. The flow rate was 0.5 ml/min. DPM were determined with an on line scintillation counter. Reference retinoids were the all-trans forms of 0: 3,4-didehydroretinoic acid, 1: all-trans-retinoic acid 2: 3,4-didehydroretinol 3: retinol 4: retinyl linoleate 5: retinyl oleate 6: retinyl palmitate. Shaded area corresponds to P3. Cross-hatched area corresponds to P1

Figure 8:
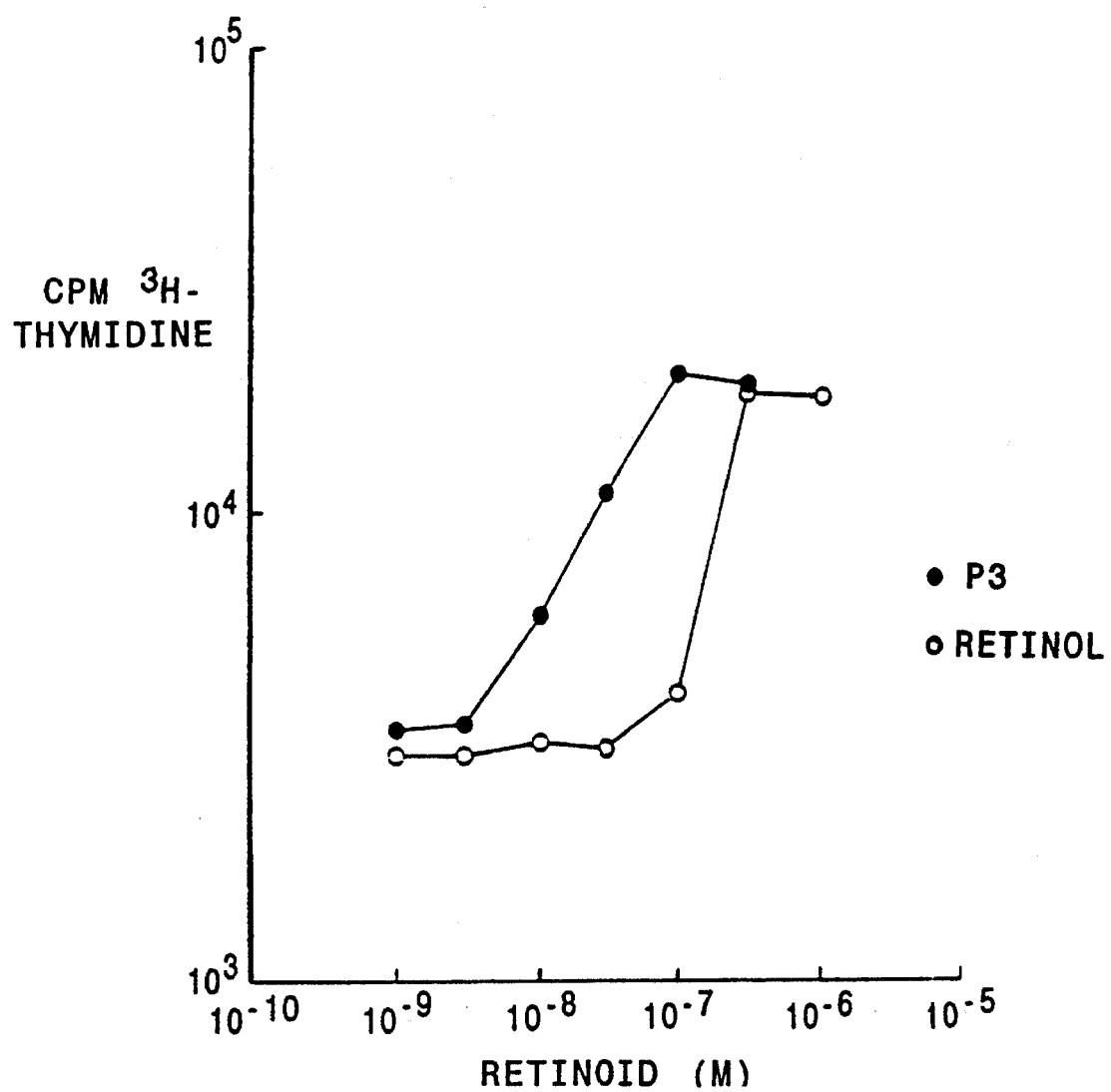

FIG. 8 shows the dose-response curve of P3 and retinol.

P3 was purified as described in the Materials and Methods section of the Detailed Description. 5/2 cells (5,000/well) were incubated for 72 hours in HB101 medium and refed with the indicated amount of retinoid daily. DNA synthesis was measured by [$^3$H]-thymidine uptake. P3 is bioactive down to a concentration of $10^{-8}$M (FIG. 8). It is 10 to 15 times more potent than retinol, but unlike with retinol, cultures have to be replenished daily with P3. This is due either to chemical instability or to a more rapid metabolic degradation of P3 by the cells.

The use of $^3$H retinol bound to fetal calf serum was used as an assay to test for P3 in other cell lines. All 26 mammalian cells tested results of 13 cells lines shown in Table 1, radioactivity peak at the position where P3 normally elutes. In the instances tested, the material in this peak also showed the characteristic UV spectrum of P3.

Figure 9A:
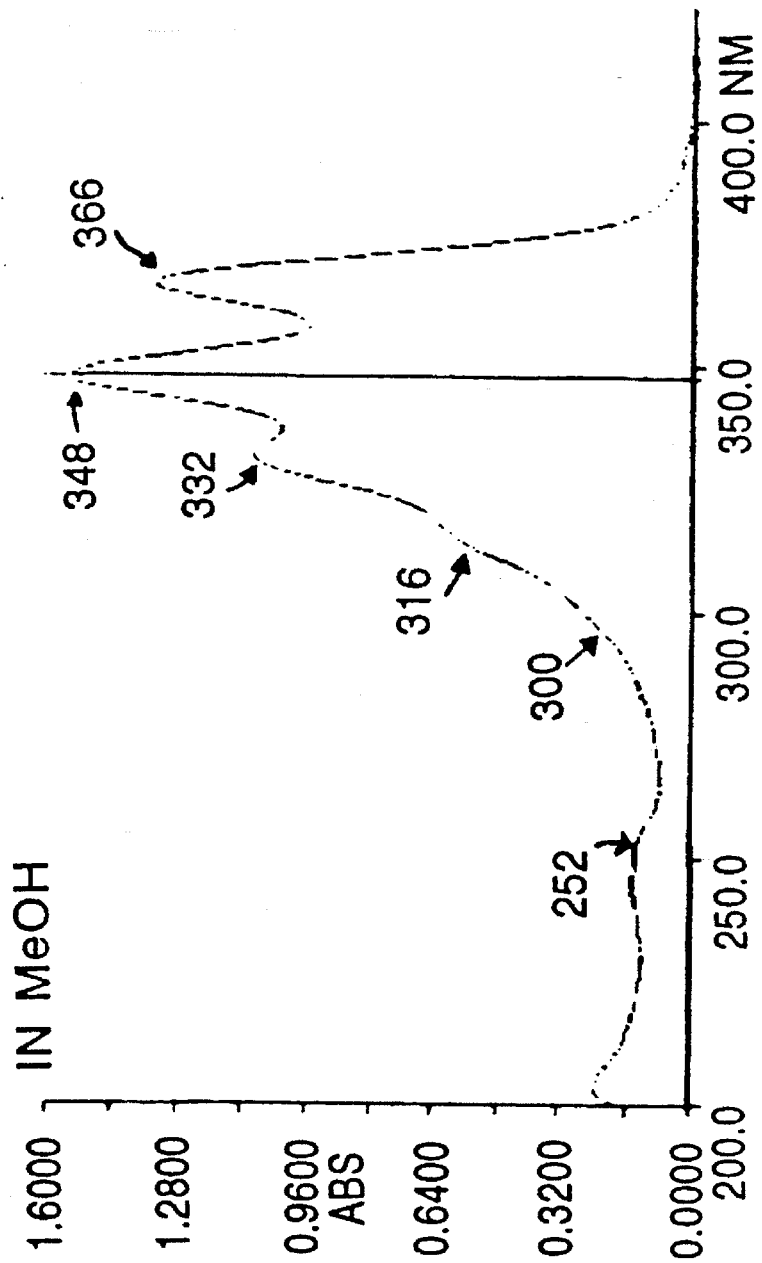
Figure 9B:
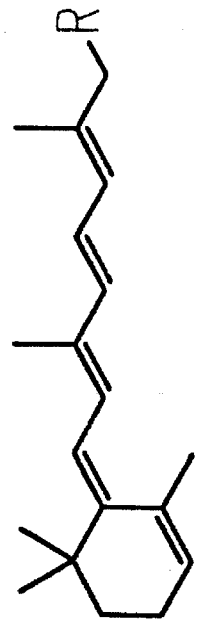
Figure 9B:
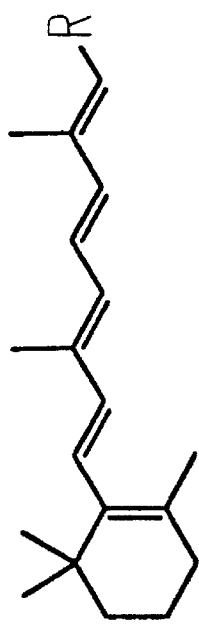
Figure 9B:
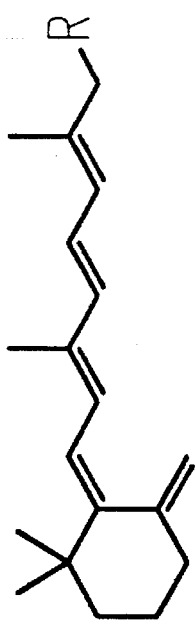

FIG. 9A shows the absorption spectrum of P3 in methanol, measured on the Perkin-Elmer Model Lambda 4B UV/VIS spectrophotometer. P3 has a λmax at 348 nm, a vibronic fine structure at 366, 332,316 and 300 nm, and a weak absorption at 252 nm. Retinoids show a fine structure in their absorption spectra when the molecule adopts a ring/side-chain planar geometry, either imposed by protein/retinoid interaction as in the retinol/CRBP complex or (9A) by a retro-configuration of the double bond system as shown in FIG. 9B (9B, 9C). Since P3 maintains its fine structure after the lipid/protein separation, protein/retinoid interaction are excluded.

Figure 10:
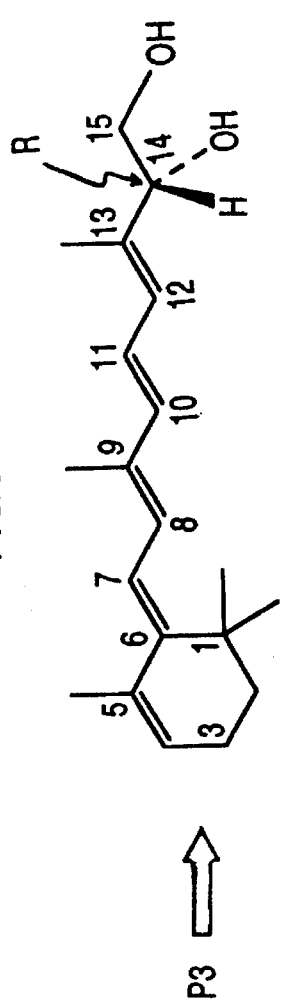
Figure 10:
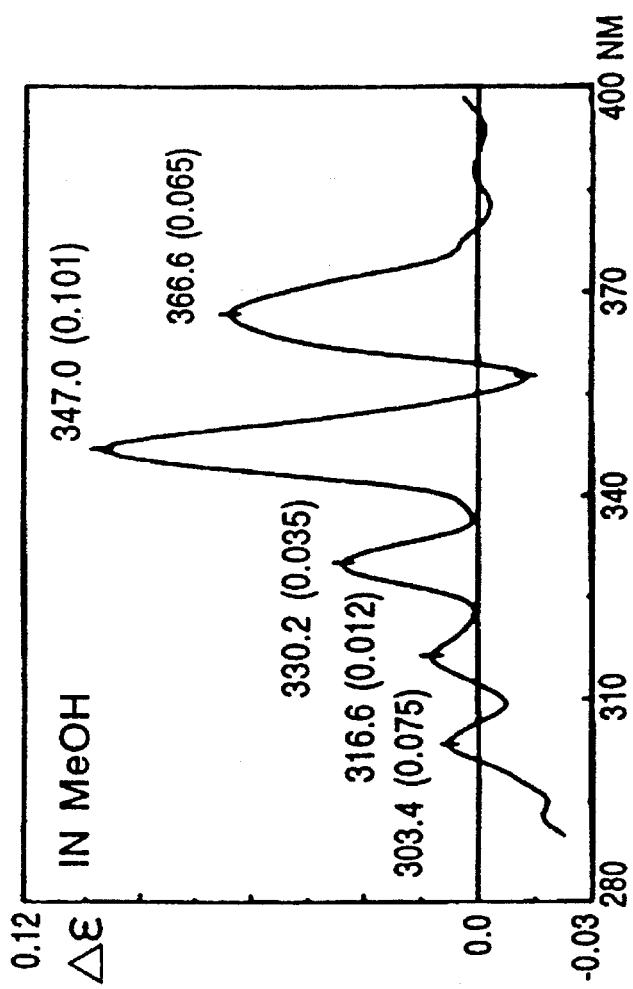

FIG. 10 shows circular dichroism spectrum of P3 on the Jasco J-720 spectropolarimeter. The CD spectrum of P3 exhibits a positive Cotton effect and fine structure. This confirms the presence of an assymeric center. The absolute configuration at C-14 is assigned as R on the basis of the positive Cotton effects associated with respective fine structured UV absorption, i.e., "allylic Hydroxyl effect" (12, 13, 14).

However, since this interpretation is dependent on the perturbation of the pentaene absorption at 348 nm by the hydroxyl group, ca. 200 nm (remote from 348 nm), and furthermore, since an additional 15-OH group is present, the configuration at C-14 needs to be confirmed by ongoing synthesis.

Figure 11A:
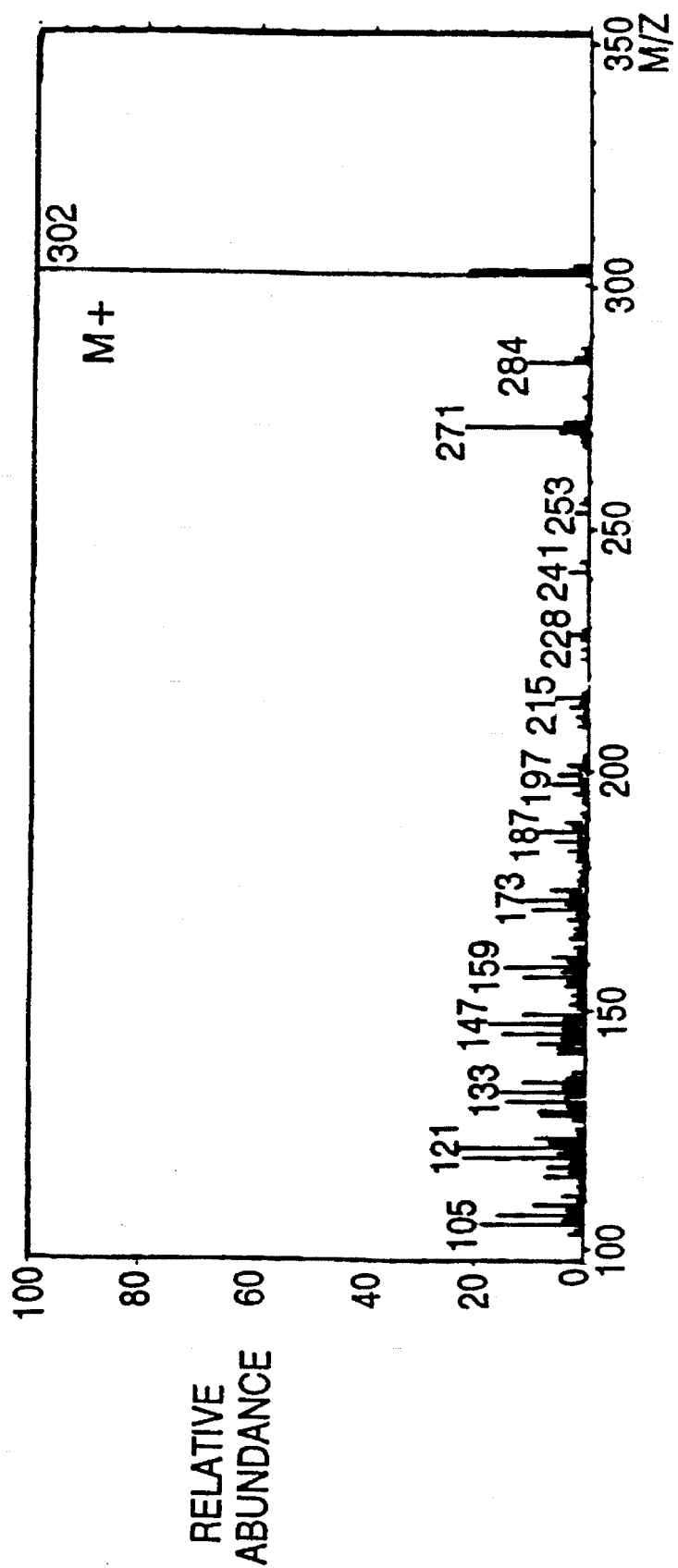

FIG. 11A shows the low resolution EI mass spectrum of P3, measured on JEOL DX-303 HF.

Low resolution EI/MS of P3 measured on JEOL DX-303 HF m/z 302 (M+ 100), 284 (11; M-H$_2$O), 271 (23; M-CH$_2$OH), 253 (2), 241 (4), 228 (4), 215 (6), 197 (6), 187 (9), 173 (10), 159 (15), 147 (17), 133 (15), 121 (23), 105 (20). The low resolution mass spectrum indicates the presence of a single compound with a molecular mass of 302 daltons.

Figure 11B:
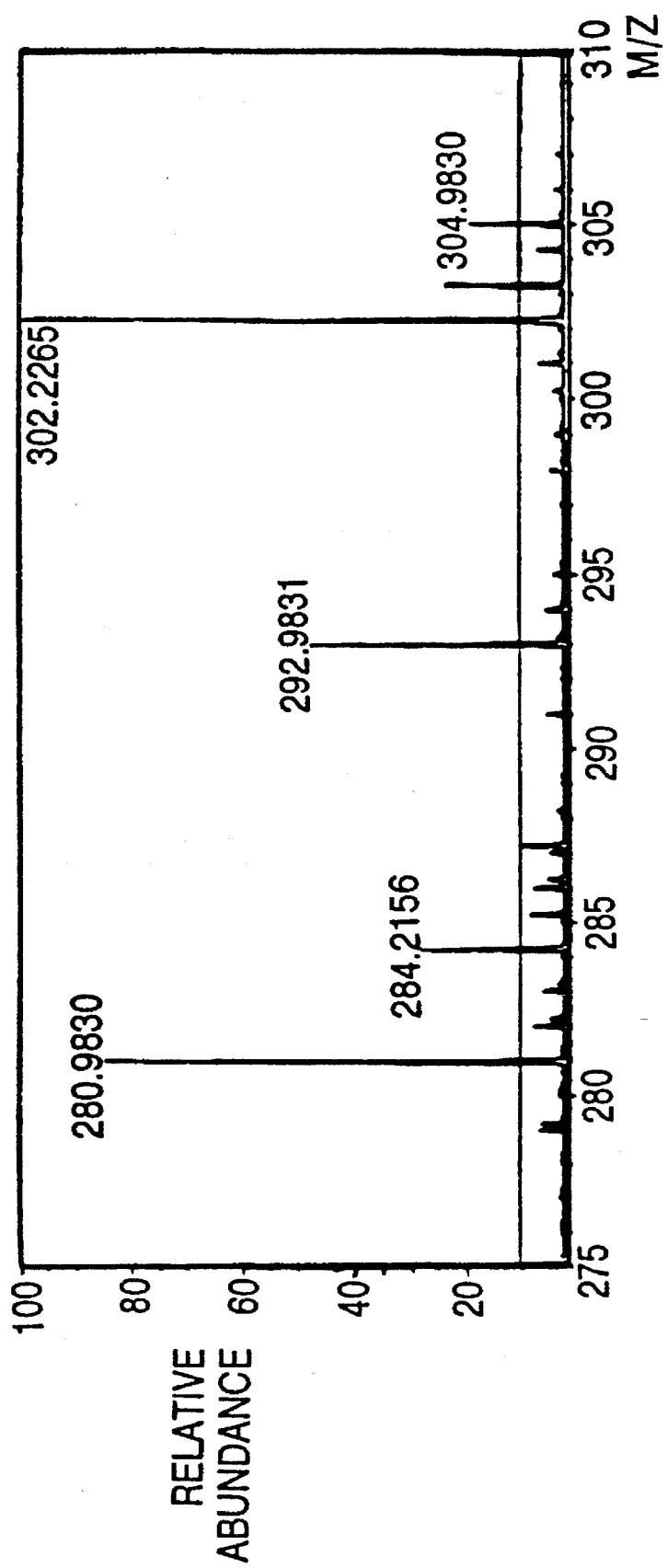

FIG. 11B shows the high resolution EI/MS (matrix PFK). The observed mass of 302.2265 (calc. 302.2246) is consistent with an atomic composition of $C_{20}H_{30}O_2$. This means that P3, which has a retro structure skeleton as suggested by absorption spectroscopy, possesses an additional oxygen atom as compared to its precursor retinol.

FIG. 12 shows proton NMR studies that established that P3 is a 14-hydroxy-retro-α-retinol. The NMR spectrum assignment was carried out by decoupling experiments and comparison with literature data given for retro-α-retinylacetate (2).

Figure 12A:
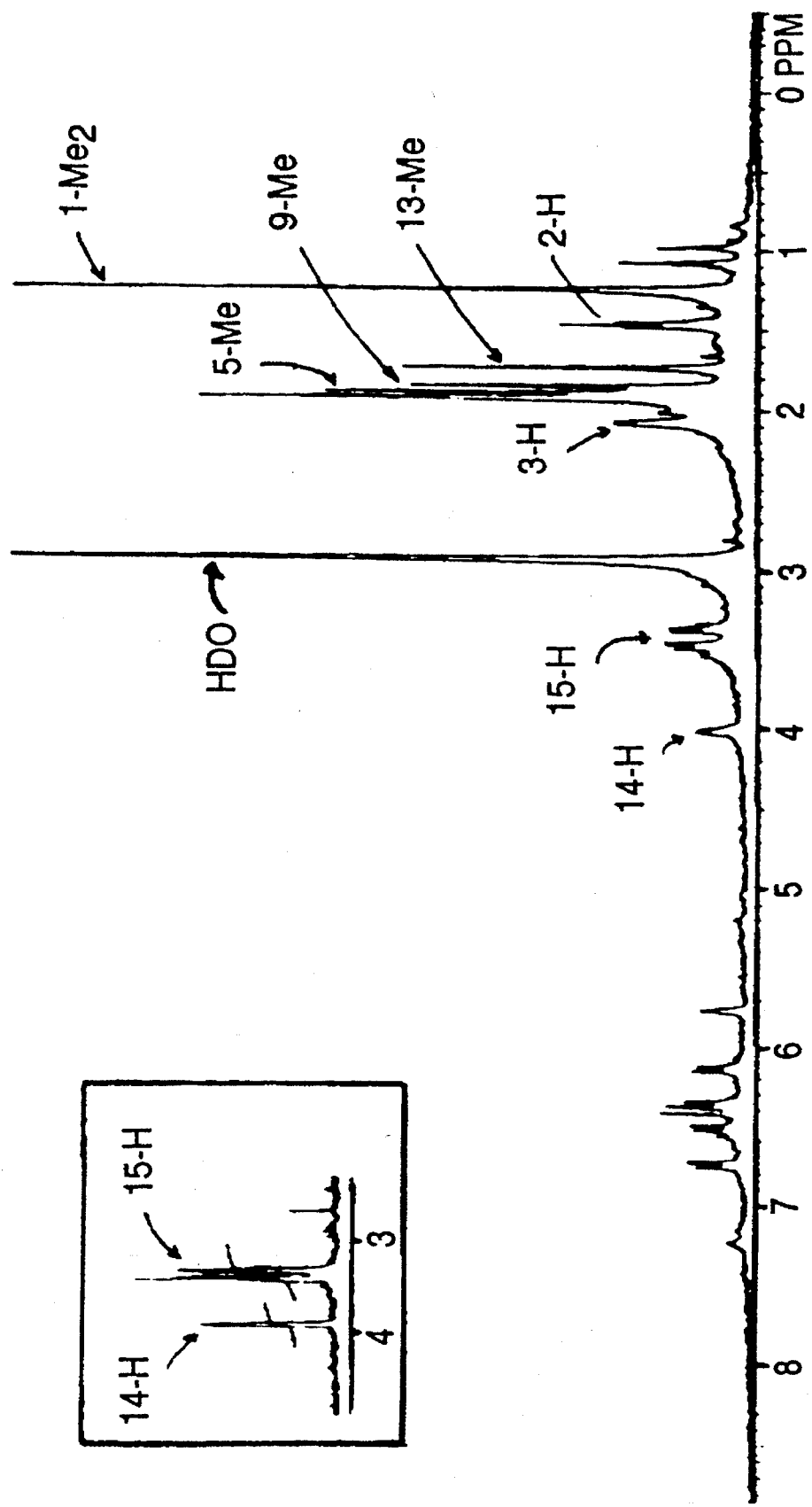

FIG. 12A shows $^1$H NMR (CD$_3$CN, VARIAN vxr-400) §1.30 (S 1-(CH-$_3$)2), 1.50 (t,J 7.5 Hz, 2-CH$_2$), 1.76a (a, 13-CH3, 1.87a (a, 9-CH3), 1.90b (a, 5-CH3), 2.08 (m, 3-CH2), 3.4 and 3.5 (2m, 15-CH2), 4.02 (m, 14-CH), 5.79 (t, J 4 Hz, 4-CH), 6.17 (d, J 12 Hz, 12-CH), 6.38 (d, J 12.3, 7-CH), 6.42 (d, J 17, 10-CH), 5.56 (dd, J 17, 12 Hz, 11-CH), 6.76 (d, J 12.3, 8-CH).

Figure 12B:
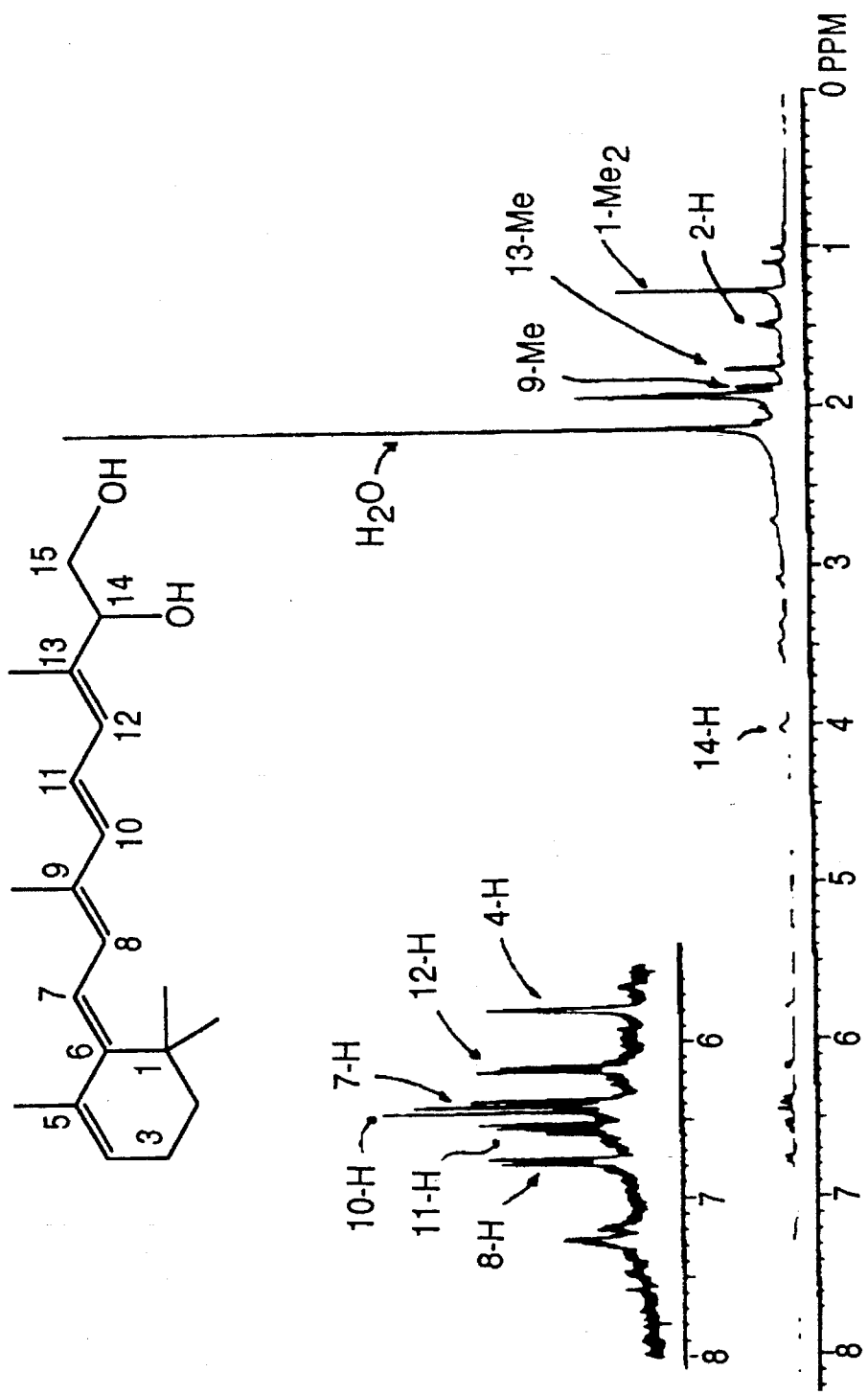

FIG. 12B shows $^1$H NMR of P3 in CD3CN after addition of few drops D20; insert shows 14-CH and 15-CH2 signals in C6D6.

The 5-Me signal at 1.90 ppm, in FIG. 12A is masked by the CH3CN multiplet at 1.93 ppm; however upon addition of few drops of D$_2$O to the sample, the latter signal shifts downfield, unmasking the 5-Me singlet (FIG. 12B). The 9-Me and 13-Me assignments are uncertain and have to be confirmed by synthesis.

The position of the 6–7 was established as E by comparison of the chemical shifts of 1-(Me (1,30), 5-Me (1.90) and 4-H (5.79) with those reported for 6-E-retro-α-retinyl acetate (15), 1.28, 1.91, 5.76 respectively. The corresponding signals for 6-Z-retro-α-retinyl acetate, are 1.11, 2.06 and 5.63. Furthermore the 6-E configuration of P3 was confirmed by observation of NOE (ca. 4%) between 1-(Me)2 and 8-H. The configuration of the 12–13 double bond, is to be confirmed by ongoing synthesis.

Figure 13:
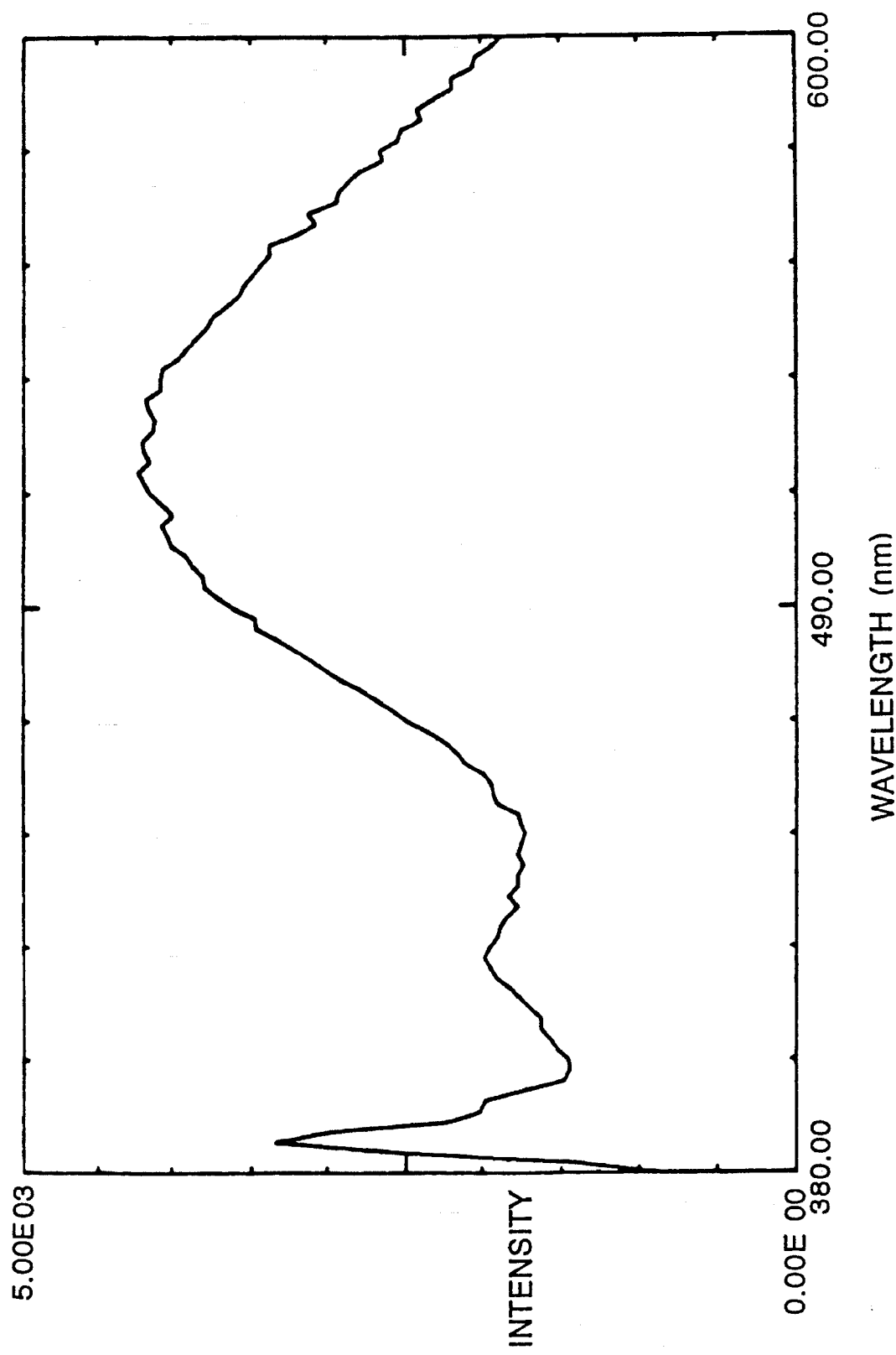

FIG. 13 shows the fluorescent emission spectrum of P3.

DETAILED DESCRIPTION OF THE INVENTION

This invention provides a purified retro-retinoid compound characterized by a molecular mass of about 302 daltons. The purified retro-retinoid compound of this invention is characterized by a compound having the atomic composition $C_{20}H_{30}O_2$ and having the structure:

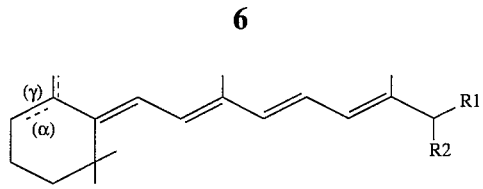

wherein the configuration of the C6, C8, C10 and C12 double bond independently is Z or E; and R$_1$ is CH$_2$OH and R$_2$ is OH. However, in the preferred embodiment, the C6 double bond is trans. As used herein, the term "compound" shall mean all isomeric forms of the above compound as well as all homologs and analogs thereof. This compound may be purified from natural sources or chemically synthesized.

This invention also provides a pharmaceutical composition which comprises the purified retro-retinoid compound described hereinabove or alternatively, a synthetic product of the compound, and a pharmaceutically acceptable carrier. As used herein, the term "pharmaceutically acceptable carrier" encompasses any of the standard pharmaceutically carriers, such as a phosphate buffered saline solution, water, and emulsions such as an oil/water emulsion, and various types of wetting agents. In the preferred embodiment of the invention, the pharmaceutically acceptable carrier also comprises specific binding proteins, which may be, but are not limited to retinol binding protein (RBP), transthyretin (TTR), the complex formed by RBP and TTR, and albumin. Most specifically, the complex composition shall have a ratio of 4:1:1 with respect to RBP, TTR and the retro-retinol compound and a concentration of about 10 to about 100 μg/ml. Albumin is at a concentration of 1 microgram per milliliter.

This invention also provides a method for obtaining the purified retro-retinoid compound described hereinabove which comprises growing a suitable cell line under suitable conditions, contacting the grown cells with $10^{-5}$M all-trans retinol, extracting the cell pellet or the culture fluid with organic solvents such as, but not limited to, butanol, acetonitrile ethyl ether, chloroform, methylene chloride, separating the organic phase from the cell pellet or culture fluid, and isolating the retro-retinoid compound by HPLC column chromatography, wherein the retro-retinoid compound elutes on a C-18 column at 83% methanol/17% water.

In the preferred embodiment of this invention, the suitable cell line is a HeLa cell line, although other mammalian and avian cell lines, such as lymphoid cells, fibroblasts, myeloid, neuroblastoma, teratoma, hepatoma and breast carcinoma can also be utilized in this method. With respect to the malignant or transformed cell lines listed above, the "normal" or non-transformed or malignant line also is useful in this method. Cell should be grown in a nutrient medium such as Eagles modified medium containing 10% bovine serum. All-trans retinol is then added. The cells are then separated from the liquid medium and washed with a neutral solution such as phosphate buffered saline (PBS). Cells should then be resuspended in the neutral solution and an organic solvent such as butanol/acetonitrile is added. The cells should be vortexed and saturated K$_2$HPO$_4$ is added. The cells are again vortexed and the organic phase should be separated. The compound is then isolated by a run through C-18 column preequilibrated with water, and run through with a gradient of methanol/water to yield the compound at 83% methanol/ 17% water.

Also provided by this invention is the compound described above as well as all isomeric forms of the above compound, and homologs and analogs thereof. This compound may be administered in a pharmaceutically acceptable carrier. As used herein, the term "pharmaceutically acceptable carrier" encompasses any of the standard pharmaceutically carriers, such as a phosphate buffered saline solution, water, and emulsions such as an oil/water emulsion, and various types of wetting agents. In the preferred embodiment of the invention, the pharmaceutically acceptable carrier also comprises specific binding proteins, which may be, but are not limited to retinol binding protein (RBP), transthyrein (TTR), the complex formed by RBP and TTR, and albumin. Most specifically, the complex composition shall have a ratio of 4:1:1 with respect to RBP, TTR and the retro-retinol compound and a concentration of about 10 to 100 μg/ml. Albumin is at a concentration of 1 microgram per milliliter.

This invention further provides a method of enhancing the growth of a cell in a vitamin A reduced environment which comprises contacting a cell with an effective growth enhancing amount of a compound having the structure:

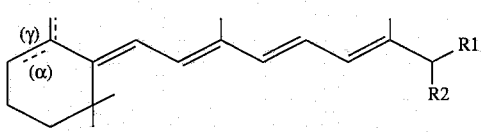

wherein the configuration of the C6, C8, C10 and C12 double bond independently is Z or E and the absolute configuration at C-14 is independently R or S; wherein $R_1$ is alkyl, alkyl halide, alcohol, ester, ether, aldehyde, ketone, carboxylic acid, carboxylic ester, acid halide, amide, nitrile, or amine; and wherein $R_2$ is hydroxyl, halide, alkoxy, ester, alkyl, alcohol, ether, aldehyde, ketone, carboxylic acid, carboxylic ester, nitrile, amine, azide, alkyl halide, acid halide, acid azide, or amide; or wherein $R_1$ and $R_2$ are replaced by a 14, 15-oxirane group; and wherein the retro structure is alpha or gamma.

As used herein, the term "enhancing the growth of a cell" means an increase of its proliferation, i.e., an increase in the cell number as a consequence of cell division. In addition, the term "vitamin A reduced environment" shall mean culture medium containing less than about $10^{-7}$ M vitamin A.

The method may be practiced in vitro or in vivo. If the method is practiced in vitro, contacting may be effected by incubating the cells with the compound. The concentration of the compound is the concentration which is effective to enhance the growth of the cell as described in FIG. 8. Therefore, the effective amount is varied with the type of cell.

Another factor in determining the effective amount of the compound is the degree of vitamin A deficiency in the environment. Thus, the effective concentration of each compound will also vary with the degree of vitamin A deficiency within the cell and the amount of compensation which is to be provided by the compound.

The method of the present invention is also intended for the treatment of animals, e.g. mammals, including human patients. When the compound is to be administered in vivo, it is intended that the compound be administered as a composition comprising the compound in a pharmaceutically acceptable carrier.

Methods of the administration to animals are well known to those of skill in the art and include, but are not limited to, administration, intravenously or parenterally. Administration of the composition will be in a dosage such that the compound enhances the growth of the cell to be effected. Administration may be effected continuously or intermittently such that the amount of the composition in the patient is effective to enhance the growth of the target cell to be effected.

In the preferred embodiment of this invention, $R_1$ is $CH_2OH$ and $R_2$ is —OH, and the C6 double bond is trans. In addition, administration of the compound is effected continuously.

This invention also provides a method for enhancing transcription of a gene regulated by retinoids in any cell which comprises contacting the cell with an effective transcription enhancing amount of a compound having the structure:

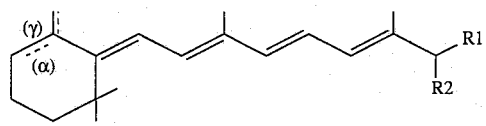

wherein the configuration of the C6, C8, C10 and C12 double bond independently is Z or E and the absolute configuration at C-14 is independently R or S; wherein $R_1$ is alkyl, alkyl halide, alcohol, ester, ether, aldehyde, ketone, carboxylic acid, carboxylic ester, acid halide, amide, nitrile, or amine; and wherein $R_2$ is hydroxyl, halide, alkoxy, ester, alkyl, alcohol, ether, aldehyde, ketone, carboxylic acid, carboxylic ester, nitrile, amine, azide, alkyl halide, acid halide, acid azide, or amide; or wherein $R_1$ and $R_2$ are replaced by a 14, 15-oxirane group; and wherein the retro structure is alpha or gamma.

As used herein, the term "enhancing transcription of a gene" is defined as the accelerated production of messenger RNA in cells. C-fos and CD-38, are two examples of genes which are regulated by retinol and therefore, whose transcription may be enhanced by the use of the claimed method.

As used herein, the term contacting, is to mean contacting in vitro or in vivo. Methods of in vitro and in vivo contacting are described hereinabove. The effective amount of a compound is the amount which enhances transcription of certain genes in the cell and will vary with the type of cell as well as the gene to be regulated. Methods of determining the effective amount are well known to those of skill in the art.

This invention also provides a method for enhancing an immune response which comprises administering to the subject an effective immune-enhancing amount of a compound having the structure:

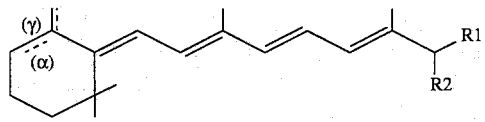

wherein the configuration of the C6, C8, C10 and C12 double bond independently is Z or E and the absolute configuration at C-14 is independently R or S; wherein $R_1$ is alkyl, alkyl halide, alcohol, ester, ether, aldehyde, ketone, carboxylic acid, carboxylic ester, acid halide, amide, nitrile, or amine; and wherein $R_2$ is hydroxyl, halide, alkoxy, ester, alkyl, alcohol, ether, aldehyde, ketone, carboxylic acid, carboxylic ester, nitrile, amine, azide, alkyl halide, acid halide, acid azide, or amide; or wherein $R_1$ and $R_2$ are replaced by a 14, 15-oxirane group; and wherein the retro structure is alpha or gamma and a pharmaceutically acceptable carrier. In the preferred embodiment of this invention, $R_1$ is $CH_2OH$ and $R_2$ is —OH and the C6 position is trans. This method is effective for enhancing the subject's cellular immune response as well as the subject's humoral immune response. As used herein, the definition of the terms "cellular immune response" and "humoral immune response" are known to those of skill in the art. For the purposes of this invention, the subject may be, but is not limited to, an animal, such as a mammal, or a human patient.

It is contemplated that this invention is to be practiced in vivo. Accordingly, an effective amount is an amount which is effected to enhance the immune response of the subject. Accordingly, the effective amount will vary with the subject being treated, as well as the condition to be treated. For the purposes of this invention, the methods of administration are to include, but are not limited to, administration intravenously or parenterally.

This invention is illustrated in the Materials and Methods section which follows. This section is set forth to aid in an understanding of the invention but is not intended to, and should not be construed to, limit in any way the invention as set forth in the claims which follow.

MATERIALS AND METHODS

Retinoids

Ro-10-1670 (Etretine, Ro 13-7410 (TTNPB), Ro 40-6085 (AM 80), and 3,4,-didehydroretinol were generous gifts of Hoffman-LaRoche, Inc. Nutley, N.J. 3,4-didehydroretinol was oxidized to 3,4-didehydroretinal and 3,4-didehydroretinoic acid according to the procedure of Mayer et al. (3). Retinyl esters were a gift of Dr. W. Blaner, Columbia University, N.Y. All other unlabeled retinoids used were purchased from Sigma Chemical Co. (St. Louis, Mo.). [$^3$H] retinol was purchased from Amersham, Arlington Heights, Ill. and was >98% pure according to HPLC analysis. The retinoids were dissolved in methanol/chloroform (3:1) (vol/vol) at a concentration of $3\times10^{-2}$M with $10^{-4}$M butylated hydroxytoluene (BHT) (Sigma Chemical Co.) added and stored in the dark at −20° C. in a nitrogen atmosphere. Immediately before bioassays, the stock solutions were diluted in serum-free medium.

Cell Lines

The human EBV-transformed B-cell line 5/2 was established from the peripheral blood of a healthy donor. The cell line was grown in RPMI 1640 supplemented with 8% fetal calf serum, L-glutamine (2 mM), and antibiotics. The cell line was tested regularly for mycoplasma infections and was consistently negative.

Synthesis of Retroretinol

Retroretinol is prepared by treatment of retinal enolacetate with NaBH$_4$, and can be converted to retroretinyl acetate by acetylation of retroretinol (16). Retroretinyl acetate has also been prepared by treatment of retinyl acetate with aqueous HBr (17). Retrovitamin A methyl ether was synthesized in 1952 (18). Derivations of the above may be synthesized by methods well known to those of skill in the art.

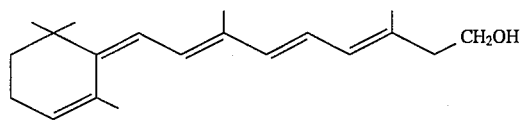

RETRORETINOL

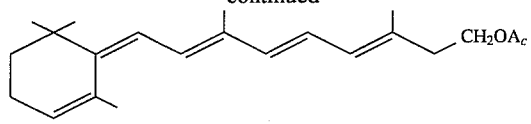

RETRORETINYL ACETATE

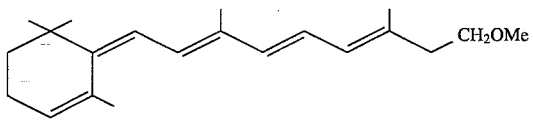

RETROVITAMIN A METHYLETHER

Chemical Synthesis of P3

Compound #2 (below) is prepared from 2,6,6-trimethyl-cyclohexenone 1 according to methods well known by those of skill in the art (19). Intermediate #3 is synthesized from commercially available (R) or (S) glyceraldehyde.

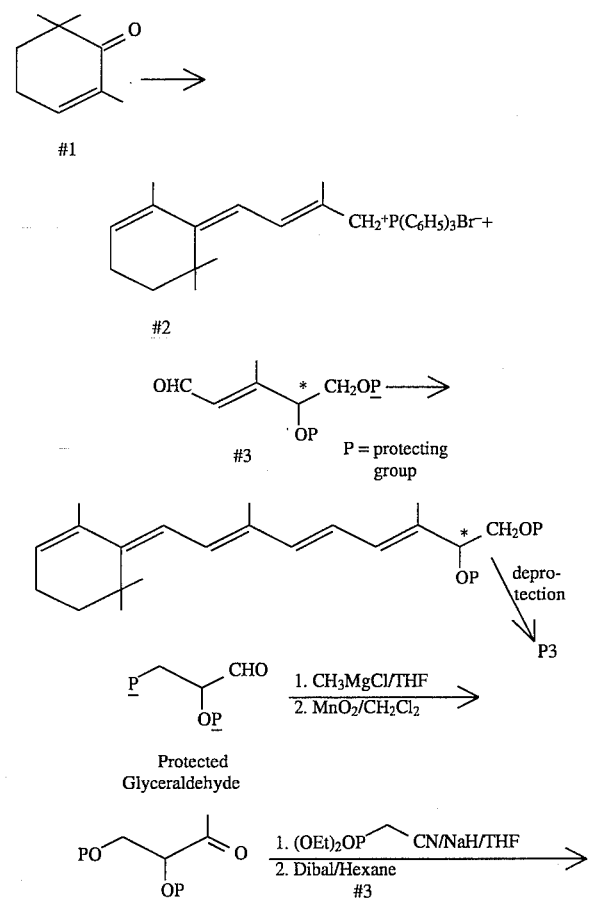

Cell Proliferation Assay

The assay system is a modification of the assay developed by Blazar et al. (10). Specifically, cells taken from their exponential growth phase were washed twice and seeded with or without retinoids at graded cell concentrations in serum-free HB 101 medium (Hana Biologics, Berkeley, Calif.) or in FCS containing RPMI medium. Assays were done in 96 well microtiter plates in a final volume of 200 μl/well or in 25 cm$^2$ tissue culture flasks. The cells in the microtiter plates were cultured for 72 hours and cell growth was determined by labeling for the last 16 hours with 0.8 µCi/well of [$^3$H]thymidine (sp. act. 6.7 Ci/mmol). Growth in the culture flasks was determined in three aliquots of 100 µl taken at 24 hours intervals and cultured in the presence of 0.8 µCi of [$^3$H]thymidine for an additional 6 hour period. To determine the viable cell number, nine aliquots per time point were differentially counted in a Neubauer chamber in the presence of trypan blue.

Purification of P3

HeLa cells were grown in spinner flasks in Eagles modified medium containing 10% bovine serum to a density of $7 \times 10^5$ cells/ml. $10^{-5}$M all-trans retinol (Sigma) was added 16 hours before harvesting the cells. The cells were spun down and washed with phosphate buffered saline (PBS). 12 ml of packed cells were resuspended in 24 ml PBS and 9.6 ml-butanol/acetonitrile 1:1 (v/v) was added. After vortexing for one minute, 7.2 ml of a saturated $K_2HPO_4$ was added. The mixture was vortexed again for one minute, and the organic phase were separated by centrifugation at 8000 rpm for 10 minutes.

The organic phase was diluted with an equal volume of water and loaded on a preparative C-18 HPLC column (Vydac) which was preequilibrated with water. The column was eluted with a gradient of water to methanol. P3 eluted at 83% methanol/17% water as determined by the characteristic absorption spectrum in the photodiode array detector. The P3-containing fraction was rechromatographed on a semipreparative $C_{18}$ column (Vydac) using as eluant a linear gradient of water to acetonitrile. P3 eluted at 25% water, 75% acetonitrile.

To concentrate P3, the purified material from the semipreparative C18 column was loaded on an analytical C4 column (VYDAC) and eluted with a linear gradient water to methanol. P3 eluted at 28% water, 72% methanol. $10^{11}$ HeLa cells yielded 25 optical units of P3 at 348 nm. This material was analyzed by NMR.

RNA and DNA Staining

To analyze cell progression through the cell cycle, cells were stained with acridine orange (Polysciences Inc., Warrington, Pa.). In brief, 0.4 ml of acid detergent (0.1% Triton X-100; 0.08N HCl; 0.15M NaCl) was added to 0.2 ml of the cell suspension. Thirty seconds later, 1.2 ml of acridine orange staining solution (6.0 ug/ml acridine orange, $10^{-3}$M EDTA, 0.15M NaCl, 0.1 M citrate-phosphate buffer at pH 6) was added to each sample. Cells were measured immediately using a FC200 flow cytometer (Ortho Diagnostics, Westwood, Mass.) as described (17,18). The red (600 to 640 nm) and green (515 to 575 nm) luminescence emissions from each cell were optically separated, measured by separate photomultipliers, and the data collected and stored in a Compaq Deskpro 386 computer. The number of cells in $G_1$, S and $G_2$+M cell cycle compartments were calculated using interactive computer programs.

RESULTS

Lymphoblastoid 5/2 cells grown in the presence of $10^{-6}$M retinol were spiked with $^3$H-labeled retinol. After 16 hours the cell pellet was delipidated according to the method of McLean et al. and separated on a reversed phase C-18 HPLC column (FIG. 7). By comigration with standards, 13-cis retinol, all-trans retinol, and several retinyl esters were identified. Retinoic acid, 3,4-didehydroretinol acid as well as 3,4-didehydroretinol were not detectable. Three peaks, P1, P2 and P3, could not be immediately identified. One peak eluting at 36–39 minutes (corresponding 83% methanol 7% water) called P3, was unusual because unlike P1 eluting at 31–34 minutes, its relative amount increased when the retinol concentration was lowered or when retinol was given to the cells bound to RBP. P3 was tested in the B-cell growth assay and found it was active and capable of replacing retinol (FIG. 8). Since HeLa cells contain P3, these cells were also used. 50 ml of packed HeLa cells ($10^{10}$ cells) yielded 25 $OD_{348nm}$ units of pure P3 after the following sequence of steps: 1. Growth in the presence of $10^{-5}$ M retinol; 2. Extraction of cell pellet according to McClean et al. (11); 3. Preparative C-18 HPLC column eluted with a water/methanol gradient; 4. semipreparative $C_{18}$ HPLC column eluted with a water/acetonitrile gradient; 5. analytical $C_4$ column eluted with a water/methanol gradient. P3 is unstable in chloroform and does not survive an acid extraction step. P3 displayed an absorption with a fine structure and absorption maxima at 326.

An EI mass spectrum of P3 was obtained. This spectrum (FIG. 11B) indicated the presence of a compound with a molecular mass of 302 daltons. High resolution mass spectroscopy showed a mass of 302.2265, which is consistent with an atomic composition of $C_{20}H_{30}O_2$. This means that P3 not only has a retro structure but an additional oxygen atom as compared with its precursor retinol.

Proton NMR confirmed the features of 14-hydroxy-retro-α-retinol structure. P3 is bioactive down to a concentration of $10^{-8}$M. It is 10 to 15 times more potent than retinol on a molar basis, but unline retinol, cultures have to be replenished daily with P3. This is due either to chemical instability or to a more rapid metabolic degradation of P3 by the cells.

The use of $^3$H retinol bound to fetal calf serum was used as an assay to test for P3 in other cell lines. All 26 mammalian cells tested results of 13 cells lines shown in Table 1, radioactivity peak at the position where P3 normally elutes. In the instances tested, the material in this peak also showed the characteristic UV spectrum of P3.

REFERENCES

1.–3. Wolbach, S. B. et al. J. Exp. Med. 42: 753 (1925).
4. Rahmathullah, L, et al. N. Eng. J. Med. 323:929–935 (1990).
5. Buck, J. et al. J. Exp. Med. 171:1613–1624 (1990).
6. Slack, J. M. Nature (London) 327:553–554 (1987).
7A. Petkovich, M. et al. Nature (London) 330: 444–450 (1987).
7B. Giguere, V. et al. Nature (London) 330:624–629 (1987).
7C. Mangelsdorf, D. J. et al. Nature (London) 345:224–229 (1990).
8. Evans, R. M. Science 240:889–895 (1988).
9A. McDonald, P. N. and Ong, D. E. J. Biol. Chem 262:10550 (1987).
9B. T. Schreckenbach, B. Walckhoff, D. Oesterhelt, Eur. J. Biochem., 76:499–511 (1977).
9C. K. Reppe in "Houben-Weyl, Methoden der Organischen Chemie", Thieme-Verlag Stuttgart (E. Muller Ed.), Vol. V 1d:7–31 (1970).
10. Blazar, B. A. et al. Cancer Res. 43:4562 (1983).
11. McLean, et al. Clin. Chem. 28:693–696 (1982).
12. N. C. Gonnella, K. Nakanishi, V. S. Martin, K. B. Sharpless, J. Am. Chem. Soc., 104:3775–3776 (1982).
13. S. Natori, in "Natural Products Chemistry", K. Kakanishi et al., Eds. Vol. I, Kodansha Ltd., Tokyo, Academic Press, Inc. New York, N.Y., pp. 30–32 (1974).

14. A. F. Beecham, Tetrahedron, Vol. 27:5207 (1971).
15. W. Vetter, et al., in "Carotenoids", O. Isler Ed. Berkhauser Verlag Basel, 204–243 (1971).
16. L. Gosswein, 1976, Diplomarbeit. Univ. of Wurzburg.
17. R. H. Beutel et al., J. Am. Chem. Soc. 77:5166–5167 (1955).
18. W. Oroshnik, et al. J. Am. Chem. Soc. 74: 295–304 (1952).
19. H. Mayer et al. Helv. Chim. Aca. 50: 1606–1619 (1967).

TABLE I

| Cell type cts. | Line | P3(%) | Retinol (%) | Ester (%) | Total |
|---|---|---|---|---|---|
| Burkitt's lymphoma-human | | | | | |
| ×10⁵ | Raji 4° | 0 | 99 | 0 | 2.5 |
| ×10⁵ | Raji 37° | 3 | 79 | 14 | 4.0 |
| Lymphoblastoid cells-human | 5/2 | 4 | 67 | 24 | 5.7 |
| Lymphoblastoid cells-human | Ket | 3 | 52 | 41 | 4.6 |
| ×10⁵ | | | | | |
| Leukemia (ALL) ×10⁵ human | SKL3 | 2 | 71 | 24 | 1.6 |
| Leukemia (ALL) ×10⁵ human | RPMI | 2 | 58 | 38 | 1.2 |
| Leukemia, pre-B ×10⁵ mouse | SLA | 3 | 85 | 9 | 6.1 |
| Leukemia, T-Cell ×10⁵ mouse | EL-4 | 5 | 40 | 44 | 2.8 |
| Leukemia, T-Cell ×10⁵ mouse | ERLD | 9 | 63 | 20 | 2.8 |
| Monocytic ×10⁵ leukemia mouse | P388D.1 | 0.5 | 71 | 26 | 1.4 |
| B-cell hybridoma ×10⁵ | SK3886 | 3 | 92 | 2 | 4.7 |
| Cervical ×10⁵ carcinoma-human | Hela | 3 | 71 | 20 | 1.0 |
| Teratocarcinoma ×10⁵ human | N-tera2 | 0.4 | 0.7 | 97 | 13.5 |
| Neuroblastoma ×10⁵ human | SK-N-SH | 0.9 | 56 | 25 | 2.0 |

Legend: 2.5 × 10⁶ cells were grown overnight in 5 ml RPMI/10% FBS. The FBS was preincubated at room temperature with 14.4 uCi [³H] retinol (NEN) for 4 h. The cell pellet was washed twice with PBS. The retinoid were extracted according to MClean et al. 90 and separated on an analytical $c_{18}$ reverse phase column according to FIG. 7. The DPM were determined using an on-line scintillation counter.

What is claimed is:

1. A homogeneous retro-retinoid compound having the retrostructure:

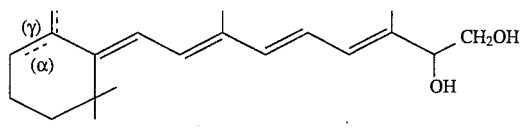

where the configuration of the double bond at C6, C8, C10 and C12 is independently Z or E; and wherein the retro structure is (α) or (γ).

2. The homogeneous retro-retinoid compound of claim 1, wherein the double bond at C6 is E.

3. A pharmaceutical composition which comprises the homogeneous retro-retinoid compound of claim 1 and a pharmaceutically acceptable carrier.

4. A method for obtaining the homogenous retro-retinoid compound of claim 1 which comprises:

a) growing HeLa cells in Eagles modified medium containing 10% bovine serum to a density of 7×10⁵ cells/ml;

b) adding $10^{-5}$M all-trans retinol to the growing cells 16 hours before harvesting the cells;

c) recovering the cells;

d) resuspending the cells so recovered in phosphate buffered saline;

e) adding butanol/acetonitrile 1:1 (v/v) to the resuspended cells;

f) adding saturated $K_2HPO_4$ to the resuspended cells from step (e);

g) separately recovering the organic phase from step (f); and h) purifying the retro-retinoid compound from the organic phase by HPLC chromatography on a C-18 column, the compound eluting at 83% methanol/17% water when eluted with a gradient of water to methanol, followed by HPLC chromatography on a second C-18 column, the compound eluting at 25% water/75% acetonitrile when eluted with a linear gradient of water to acetonitrile.

* * * * *